US006235514B1

(12) United States Patent
Croteau et al.

(10) Patent No.: US 6,235,514 B1
(45) Date of Patent: May 22, 2001

(54) NUCLEIC ACID MOLECULES ENCODING ISOPENTENYL MONOPHOSPHATE KINASE, AND METHODS OF USE

(75) Inventors: Rodney B. Croteau; Bernd M. Lange, both of Pullman, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 09/434,774

(22) Filed: Nov. 4, 1999

(51) Int. Cl.⁷ .............................. C12N 9/00; C12N 9/12; C12N 1/20; C12N 15/00; C12N 5/04
(52) U.S. Cl. .................. 435/194; 435/183; 435/252.3; 435/320.1; 435/419; 514/44; 536/23.6
(58) Field of Search ................................ 435/183, 252.3, 435/320.1, 194, 419; 514/44; 536/23.6

(56) References Cited

PUBLICATIONS

Sprenger, G.A. et al., "Identification of a thiamin–dependent synthase in *Escherichia coli* required for the formation of the 1–deoxy–D–xylulose 5–phosphate precursor to isoprenoids, thiamin, and pyridoxol," *Proc. Natl. Acad. Sci USA*, 94:12857–12862 (1997).
Lois, L.M. et al., "Cloning and characterization of a gene from *Escherichia coli* encoding a transketolase–like enzyme that catalyzes the synthesis of D–1–deoxyxylulose 5–phosphate, a common precursor for isoprenoid, thiamin, and pyridoxol biosynthesis," *Proc. Natl. Acad. Sci. USA*, 95:2105–2110 (1998).
Lange, B.M. et al., "A Family of transketolases that directs isoprenoid biosynthesis via a mevalonate–independent pathway," *Proc. Natl. Acad. Sci. USA*, 95:2100–2104 (1998).
Bouvier, F. et al., "Dedicated Roles of Plastid Transketolases during the Early Onset of Isoprenoid Biogenesis in Pepper Fruit," *Plant Physiol.*, 117:1423–1431 (1998).
Lawrence, S.D., et al., "Chromoplast development in ripening tomato fruit: identification of cDNAs for chromoplast–targeted proteins and characterization of a cDNA encoding a plastid–localized low–molecular–weight heat shock protein," *Plant Mol. Biol.*, 33:483–492 (1997).
Genbank Accession Number U62773 released on Mar. 20, 1997. Discloses nucleic acid molecule encoding putative isopentenyl monophosphate kinase from tomato (*Lycopersicon esculentum*) (the amino acid sequence of which is disclosed in the present patent application as SEQ ID No: 9).
Genbank Accession Number AC005168 released on Jun. 23, 1998. Discloses nucleic acid sequence of portion of *Arabidopsis thaliana* chromosome II that includes a nucleic sequence that encodes a putative isopentenyl monophosphate kinase (the amino acid sequence of which is highlighted in yellow) which is disclosed in the present patent application as SEQ ID No:11).
GenBank Accession Number D90756 released on Jul. 29, 1996. Discloses nucleic acid sequence of portion of *E. coli* genome that encodes a putative isopentenyl monophosphate kinase (the amino acid sequence of which is highlighted in yellow) which is disclosed in the present patent application as SEQ ID No:5).
GenBank Accession Number D90899 released on Jun. 28, 1996. Discloses complete sequence of *Synechocystis* genome including nucleic acid sequence that encodes a putative isopentenyl monophosphate kinase (the amino acid sequence of which is highlighted in yellow) which is disclosed in the present patent application as SEQ ID No:15).

*Primary Examiner*—Ponnathapu Achutamurthy
*Assistant Examiner*—Manjunath Rao
(74) *Attorney, Agent, or Firm*—Christensen O'Connor Johnson Kindness PLLC

(57) ABSTRACT

A cDNA encoding isopentenyl monophosphate kinase (IPK) from peppermint (*Mentha x piperita*) has been isolated and sequenced, and the corresponding amino acid sequence has been determined. Accordingly, an isolated DNA sequence (SEQ ID NO:1) is provided which codes for the expression of isopentenyl monophosphate kinase (SEQ ID NO:2), from peppermint (*Mentha x piperita*). In other aspects, replicable recombinant cloning vehicles are provided which code for isopentenyl monophosphate kinase, or for a base sequence sufficiently complementary to at least a portion of isopentenyl monophosphate kinase DNA or RNA to enable hybridization therewith. In yet other aspects, modified host cells are provided that have been transformed, transfected, infected and/or injected with a recombinant cloning vehicle and/or DNA sequence encoding isopentenyl monophosphate kinase. Thus, systems and methods are provided for the recombinant expression of the aforementioned recombinant isopentenyl monophosphate kinase that may be used to facilitate its production, isolation and purification in significant amounts. Recombinant isopentenyl monophosphate kinase may be used to obtain expression or enhanced expression of isopentenyl monophosphate kinase in plants in order to enhance the production of isopentenyl monophosphate kinase, or isoprenoids derived therefrom, or may be otherwise employed for the regulation or expression of isopentenyl monophosphate kinase, or the production of its products.

23 Claims, 1 Drawing Sheet

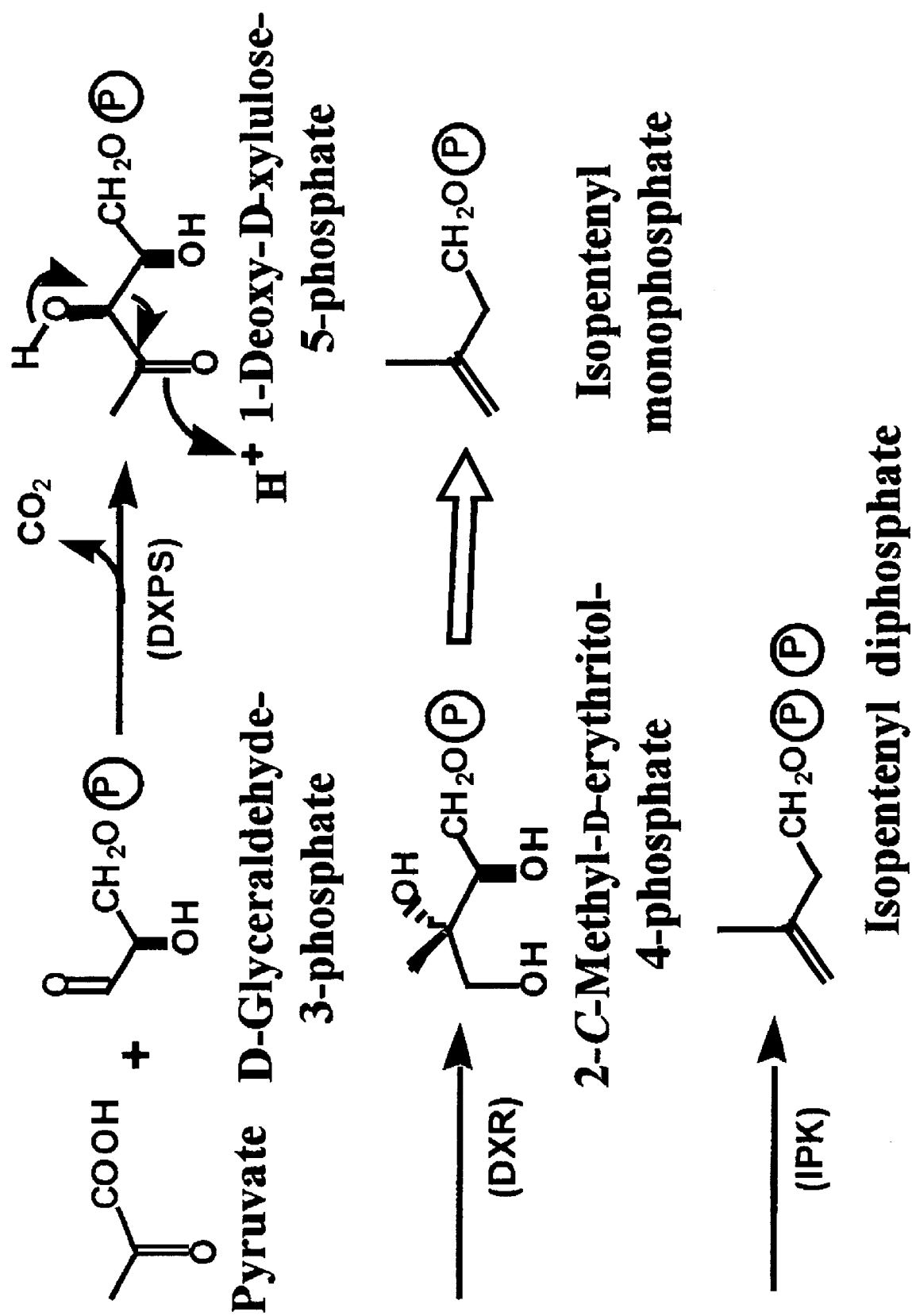

SEQUENCE LISTING

```
<160> NUMBER OF SEQ ID NOS:  16

<210> SEQ ID NO 1
<211> LENGTH: 1481
<212> TYPE: DNA
<213> ORGANISM: Mentha piperita
<220> FEATURE:
<221> NAME/KEY: CDS
<222> LOCATION: (3)..(1217)

<400> SEQUENCE: 1 ca atg gct tcc tcc tcc cat ttc ctc tac agt cac cac cat agc tac       47
   Met Ala Ser Ser Ser His Phe Leu Tyr Ser His His His Ser Tyr
     1               5                  10                  15 gct tct tac aat tcg aag tca cat ttc aat tcc ttc acc aac gcc act       95
Ala Ser Tyr Asn Ser Lys Ser His Phe Asn Ser Phe Thr Asn Ala Thr
             20                  25                  30 ttt cct caa ttc tct tcg ttt aag cct aat ggg tcg tcg tct ttt cgc      143
Phe Pro Gln Phe Ser Ser Phe Lys Pro Asn Gly Ser Ser Ser Phe Arg
         35                  40                  45 aaa aag ctt cag tct tca aga atc cat atc atc aga gcc gcg gct tct      191
Lys Lys Leu Gln Ser Ser Arg Ile His Ile Ile Arg Ala Ala Ala Ser
     50                  55                  60 gat ccc aca act ggc aga aat caa ctc gag gtg gta tat gat ctt gag      239
Asp Pro Thr Thr Gly Arg Asn Gln Leu Glu Val Val Tyr Asp Leu Glu
 65                  70                  75 aat aaa tta aac aaa tta gct gat gaa gtg gat agg gag gct ggg att      287
Asn Lys Leu Asn Lys Leu Ala Asp Glu Val Asp Arg Glu Ala Gly Ile
 80                  85                  90                  95 tca aga ctc act ctt ttt tcg cct tgc aag att aat gtt ttc tta aga      335
Ser Arg Leu Thr Leu Phe Ser Pro Cys Lys Ile Asn Val Phe Leu Arg
            100                 105                 110 ata act ggc aag aga gaa gat gga ttc cat gat ttg gcg tca ctt ttt      383
Ile Thr Gly Lys Arg Glu Asp Gly Phe His Asp Leu Ala Ser Leu Phe
        115                 120                 125 cat gtt atc agc cta gga gat aaa ata aag ttc tcg ttg tca cca tca      431
His Val Ile Ser Leu Gly Asp Lys Ile Lys Phe Ser Leu Ser Pro Ser
    130                 135                 140
```

```
aag ttc aac gga tcg ttt gtc acc aat gtc ccc gga gtt cct ctt gat      479
Lys Phe Asn Gly Ser Phe Val Thr Asn Val Pro Gly Val Pro Leu Asp
145                 150                 155 gaa aaa aat ttg ata ata aag gct ctc aat ctt ttt agg aaa aag aca      527
Glu Lys Asn Leu Ile Ile Lys Ala Leu Asn Leu Phe Arg Lys Lys Thr
160                 165                 170                 175 ggg act gac aag cac ttt tgg att cat ctt gat aag aag gtt ccg act      575
Gly Thr Asp Lys His Phe Trp Ile His Leu Asp Lys Lys Val Pro Thr
                180                 185                 190 gga gct ggg ctt ggg ggt ggc agt agc aat gct gct act gct tta tgg      623
Gly Ala Gly Leu Gly Gly Gly Ser Ser Asn Ala Ala Thr Ala Leu Trp
            195                 200                 205 gca gca aat cag ttc agt ggc tgc att gca act gaa aag gat ctt caa      671
Ala Ala Asn Gln Phe Ser Gly Cys Ile Ala Thr Glu Lys Asp Leu Gln
        210                 215                 220 gaa tgg tct gga gaa att ggc tct gat atc ccg ttc ttt ttc tct cat      719
Glu Trp Ser Gly Glu Ile Gly Ser Asp Ile Pro Phe Phe Phe Ser His
    225                 230                 235 gga gct gca tat tgt acg ggt aga gga gag gtt gta gaa gac att cca      767
Gly Ala Ala Tyr Cys Thr Gly Arg Gly Glu Val Val Glu Asp Ile Pro
240                 245                 250                 255 cca cct gta cct cgt gat ctt tct atg gtt ctc atg aag cca caa gag      815
Pro Pro Val Pro Arg Asp Leu Ser Met Val Leu Met Lys Pro Gln Glu
                260                 265                 270 gca tgt ccc act ggt gaa gtt tac aag cgt ctc cgg tta gac caa acg      863
Ala Cys Pro Thr Gly Glu Val Tyr Lys Arg Leu Arg Leu Asp Gln Thr
            275                 280                 285 agc gac att gat cca ttg gtg ttg cta gag aag ata tcg aag ggt gga      911
Ser Asp Ile Asp Pro Leu Val Leu Leu Glu Lys Ile Ser Lys Gly Gly
        290                 295                 300 atc tct cag gac gtt tgc gtt aat gat ctt gaa cct cct gct ttt gaa      959
Ile Ser Gln Asp Val Cys Val Asn Asp Leu Glu Pro Pro Ala Phe Glu
    305                 310                 315 gtg gtc ccg tca cta aaa aga ctt aaa cag cgc ata gcc gca gca ggt     1007
Val Val Pro Ser Leu Lys Arg Leu Lys Gln Arg Ile Ala Ala Ala Gly
320                 325                 330                 335 aga agc cag tat gat gct gtc ttc atg tcc gga agt ggg agc act att     1055
Arg Ser Gln Tyr Asp Ala Val Phe Met Ser Gly Ser Gly Ser Thr Ile
                340                 345                 350 gtg ggt gtg ggt tct cca gat cca cct cag ttt gtg tac gat ggc gat     1103
Val Gly Val Gly Ser Pro Asp Pro Pro Gln Phe Val Tyr Asp Gly Asp
            355                 360                 365 gag tac aaa aat att ttt ttc tca gag gcc aaa ttc atc acg cgc tct     1151
Glu Tyr Lys Asn Ile Phe Phe Ser Glu Ala Lys Phe Ile Thr Arg Ser
        370                 375                 380 gct aat cag tgg tac tcg gag cct ctc tcg aca gac gaa tca ccg tct     1199
Ala Asn Gln Trp Tyr Ser Glu Pro Leu Ser Thr Asp Glu Ser Pro Ser
    385                 390                 395 ttt cct cag gat gct gaa tgatctgtcc ctgtataata atagcagact            1247
Phe Pro Gln Asp Ala Glu
400             405 gaataataat accattatat gattacatct tttctccctt tccttcagtc agaatataca   1307
gattctgcag ccataccata tacccccttt tgtagcttgt gaaatgagaa ggcatgcata   1367
tctaattctg atattgcttc ccttaaataa acatcgtact ctcgaaactg taacacattc   1427
attttataat gattgttttt tatttgtcca tttttcaaaa aaaaaaaaaa aaaa         1481

<210> SEQ ID NO 2
<211> LENGTH: 405
```

```
<212> TYPE: PRT
<213> ORGANISM: Mentha piperita

<400> SEQUENCE: 2

Met Ala Ser Ser His Phe Leu Tyr Ser His His Ser Tyr Ala
 1               5                  10                  15

Ser Tyr Asn Ser Lys Ser His Phe Asn Ser Phe Thr Asn Ala Thr Phe
            20                  25                  30

Pro Gln Phe Ser Ser Phe Lys Pro Asn Gly Ser Ser Phe Arg Lys
        35                  40                  45

Lys Leu Gln Ser Ser Arg Ile His Ile Ile Arg Ala Ala Ser Asp
    50                  55                  60

Pro Thr Thr Gly Arg Asn Gln Leu Glu Val Val Tyr Asp Leu Glu Asn
 65                 70                  75                  80

Lys Leu Asn Lys Leu Ala Asp Glu Val Asp Arg Glu Ala Gly Ile Ser
                85                  90                  95

Arg Leu Thr Leu Phe Ser Pro Cys Lys Ile Asn Val Phe Leu Arg Ile
            100                 105                 110

Thr Gly Lys Arg Glu Asp Gly Phe His Asp Leu Ala Ser Leu Phe His
        115                 120                 125

Val Ile Ser Leu Gly Asp Lys Ile Lys Phe Ser Leu Ser Pro Ser Lys
130                 135                 140

Phe Asn Gly Ser Phe Val Thr Asn Val Pro Gly Val Pro Leu Asp Glu
145                 150                 155                 160

Lys Asn Leu Ile Ile Lys Ala Leu Asn Leu Phe Arg Lys Lys Thr Gly
                165                 170                 175

Thr Asp Lys His Phe Trp Ile His Leu Asp Lys Lys Val Pro Thr Gly
            180                 185                 190

Ala Gly Leu Gly Gly Gly Ser Ser Asn Ala Ala Thr Ala Leu Trp Ala
        195                 200                 205

Ala Asn Gln Phe Ser Gly Cys Ile Ala Thr Glu Lys Asp Leu Gln Glu
    210                 215                 220

Trp Ser Gly Glu Ile Gly Ser Asp Ile Pro Phe Phe Ser His Gly
225                 230                 235                 240

Ala Ala Tyr Cys Thr Gly Arg Gly Glu Val Val Glu Asp Ile Pro Pro
                245                 250                 255

Pro Val Pro Arg Asp Leu Ser Met Val Leu Met Lys Pro Gln Glu Ala
            260                 265                 270

Cys Pro Thr Gly Glu Val Tyr Lys Arg Leu Arg Leu Asp Gln Thr Ser
        275                 280                 285

Asp Ile Asp Pro Leu Val Leu Leu Glu Lys Ile Ser Lys Gly Gly Ile
    290                 295                 300

Ser Gln Asp Val Cys Val Asn Asp Leu Glu Pro Pro Ala Phe Glu Val
305                 310                 315                 320

Val Pro Ser Leu Lys Arg Leu Lys Gln Arg Ile Ala Ala Gly Arg
                325                 330                 335

Ser Gln Tyr Asp Ala Val Phe Met Ser Gly Ser Gly Ser Thr Ile Val
            340                 345                 350

Gly Val Gly Ser Pro Asp Pro Pro Gln Phe Val Tyr Asp Gly Asp Glu
        355                 360                 365

Tyr Lys Asn Ile Phe Phe Ser Glu Ala Lys Phe Ile Thr Arg Ser Ala
    370                 375                 380

Asn Gln Trp Tyr Ser Glu Pro Leu Ser Thr Asp Glu Ser Pro Ser Phe
385                 390                 395                 400
```

Pro Gln Asp Ala Glu
            405

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: Forward PCR primer for amplifying peppermint
      kinase gene

<400> SEQUENCE: 3
atggcttcct cctcccattt cctc                                              24

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(24)
<223> OTHER INFORMATION: reverse PCR primer for amplifying peppermint
      kinase

<400> SEQUENCE: 4
ttcagcatcc tgaggaaaag acgg                                              24

<210> SEQ ID NO 5
<211> LENGTH: 852
<212> TYPE: DNA
<213> ORGANISM: Escherichia coli
<220> FEATURE:
<221> NAME/KEY: CDS
<222> LOCATION: (1)..(852)

<400> SEQUENCE: 5

```
atg cgg aca cag tgg ccc tct ccg gca aaa ctt aat ctg ttt tta tac         48
Met Arg Thr Gln Trp Pro Ser Pro Ala Lys Leu Asn Leu Phe Leu Tyr
 1               5                  10                  15 att acc ggt cag cgt gcg gat ggt tac cac acg ctg caa acg ctg ttt         96
Ile Thr Gly Gln Arg Ala Asp Gly Tyr His Thr Leu Gln Thr Leu Phe
             20                  25                  30 cag ttt ctt gat tac ggc gac acc atc agc att gag ctt cgt gac gat        144
Gln Phe Leu Asp Tyr Gly Asp Thr Ile Ser Ile Glu Leu Arg Asp Asp
         35                  40                  45 ggg gat att cgt ctg tta acg ccc gtt gaa ggc gtg gaa cat gaa gat        192
Gly Asp Ile Arg Leu Leu Thr Pro Val Glu Gly Val Glu His Glu Asp
     50                  55                  60 aac ctg atc gtt cgc gca gcg cga ttg ttg atg aaa act gcg gca gac        240
Asn Leu Ile Val Arg Ala Ala Arg Leu Leu Met Lys Thr Ala Ala Asp
 65                  70                  75                  80 agc ggg cgt ctt ccg acg gga agc ggt gcg aat atc agc att gac aag        288
Ser Gly Arg Leu Pro Thr Gly Ser Gly Ala Asn Ile Ser Ile Asp Lys
                 85                  90                  95 cgt ttg ccg atg ggc ggc ggt ctc ggc ggt ggt tca tcc aat gcc gcg        336
Arg Leu Pro Met Gly Gly Gly Leu Gly Gly Gly Ser Ser Asn Ala Ala
            100                 105                 110 acg gtc ctg gtg gca tta aat cat ctc tgg caa tgc ggg cta agc atg        384
Thr Val Leu Val Ala Leu Asn His Leu Trp Gln Cys Gly Leu Ser Met
```

-continued

```
              115                 120                 125
gat gag ctg gcg gaa atg ggg ctg acg ctg ggc gca gat gtt cct gtc    432
Asp Glu Leu Ala Glu Met Gly Leu Thr Leu Gly Ala Asp Val Pro Val
    130                 135                 140 ttt gtt cgg ggg cat gcc gcg ttt gcc gaa ggc gtt ggt gaa ata cta    480
Phe Val Arg Gly His Ala Ala Phe Ala Glu Gly Val Gly Glu Ile Leu
145                 150                 155                 160 acg ccg gtg gat cca cca gag aag tgg tat ctg gtg gcg cac cct ggt    528
Thr Pro Val Asp Pro Pro Glu Lys Trp Tyr Leu Val Ala His Pro Gly
                165                 170                 175 gta agt att ccg act ccg gtg att ttt aaa gat cct gaa ctc ccg cgc    576
Val Ser Ile Pro Thr Pro Val Ile Phe Lys Asp Pro Glu Leu Pro Arg
            180                 185                 190 aat acg cca aaa agg tca ata gaa acg ttg cta aaa tgt gaa ttc agc    624
Asn Thr Pro Lys Arg Ser Ile Glu Thr Leu Leu Lys Cys Glu Phe Ser
        195                 200                 205 aat gat tgc gag gtt atc gca aga aaa cgt ttt cgc gag gtt gat gcg    672
Asn Asp Cys Glu Val Ile Ala Arg Lys Arg Phe Arg Glu Val Asp Ala
    210                 215                 220 gtg ctt tcc tgg ctg tta gaa tac gcc ccg tcg cgc ctg act ggg aca    720
Val Leu Ser Trp Leu Leu Glu Tyr Ala Pro Ser Arg Leu Thr Gly Thr
225                 230                 235                 240 ggg gcc tgt gtc ttt gct gaa ttt gat aca gag tct gaa gcc cgc cag    768
Gly Ala Cys Val Phe Ala Glu Phe Asp Thr Glu Ser Glu Ala Arg Gln
                245                 250                 255 gtg cta gag caa gcc ccg gaa tgg ctc aat ggc ttt gtg gcg aaa ggc    816
Val Leu Glu Gln Ala Pro Glu Trp Leu Asn Gly Phe Val Ala Lys Gly
            260                 265                 270 gct aat ctt tcc cca ttg cac aga gcc atg ctt taa                    852
Ala Asn Leu Ser Pro Leu His Arg Ala Met Leu
        275                 280
```

<210> SEQ ID NO 6
<211> LENGTH: 283
<212> TYPE: PRT
<213> ORGANISM: Escherichia coli

<400> SEQUENCE: 6

```
Met Arg Thr Gln Trp Pro Ser Pro Ala Lys Leu Asn Leu Phe Leu Tyr
  1               5                  10                  15

Ile Thr Gly Gln Arg Ala Asp Gly Tyr His Thr Leu Gln Thr Leu Phe
                 20                  25                  30

Gln Phe Leu Asp Tyr Gly Asp Thr Ile Ser Ile Glu Leu Arg Asp Asp
             35                  40                  45

Gly Asp Ile Arg Leu Leu Thr Pro Val Glu Gly Val Glu His Glu Asp
         50                  55                  60

Asn Leu Ile Val Arg Ala Ala Arg Leu Leu Met Lys Thr Ala Ala Asp
 65                  70                  75                  80

Ser Gly Arg Leu Pro Thr Gly Ser Gly Ala Asn Ile Ser Ile Asp Lys
                 85                  90                  95

Arg Leu Pro Met Gly Gly Gly Leu Gly Gly Gly Ser Ser Asn Ala Ala
            100                 105                 110

Thr Val Leu Val Ala Leu Asn His Leu Trp Gln Cys Gly Leu Ser Met
        115                 120                 125

Asp Glu Leu Ala Glu Met Gly Leu Thr Leu Gly Ala Asp Val Pro Val
    130                 135                 140

Phe Val Arg Gly His Ala Ala Phe Ala Glu Gly Val Gly Glu Ile Leu
145                 150                 155                 160
```

```
Thr Pro Val Asp Pro Pro Glu Lys Trp Tyr Leu Val Ala His Pro Gly
                165                 170                 175

Val Ser Ile Pro Thr Pro Val Ile Phe Lys Asp Pro Glu Leu Pro Arg
            180                 185                 190

Asn Thr Pro Lys Arg Ser Ile Glu Thr Leu Leu Lys Cys Glu Phe Ser
        195                 200                 205

Asn Asp Cys Glu Val Ile Ala Arg Lys Arg Phe Arg Glu Val Asp Ala
    210                 215                 220

Val Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Glu Ala Arg Gln
                245                 250                 255

Val Leu Glu Gln Ala Pro Glu Trp Leu Asn Gly Phe Val Ala Lys Gly
            260                 265                 270

Ala Asn Leu Ser Pro Leu His Arg Ala Met Leu
        275                 280

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: Forward PCR primer for amplifying E coli kinase
      gene

<400> SEQUENCE: 7
atgcggacac agtggccctc                                                    20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      oligonucleotide
<221> NAME/KEY: misc_feature
<222> LOCATION: (1)..(20)
<223> OTHER INFORMATION: reverse PCR primer for amplifying E coli kinase
      gene

<400> SEQUENCE: 8
aagcatggct ctgtgcaatg                                                    20

<210> SEQ ID NO 9
<211> LENGTH: 1203
<212> TYPE: DNA
<213> ORGANISM: Lycopersicon esculentum
<220> FEATURE:
<221> NAME/KEY: CDS
<222> LOCATION: (1)..(1203)

<400> SEQUENCE: 9 cta tgg ctt cct gta ata ttc ttt gta gtg tca aac ccc aaa ttg att         48
Leu Trp Leu Pro Val Ile Phe Phe Val Val Ser Asn Pro Lys Leu Ile
  1               5                  10                  15 ctt tta aaa aga gtt gtt ttt ttt cag tca tgg tca aat agg cca cat         96
Leu Leu Lys Arg Val Val Phe Phe Gln Ser Trp Ser Asn Arg Pro His
             20                  25                  30 ggt tca tcc tat ttt aac aag aat atc caa ttt aga aga aac agt ttt        144
```

```
         Gly Ser Ser Tyr Phe Asn Lys Asn Ile Gln Phe Arg Arg Asn Ser Phe
                      35                  40                  45 gtt att gtg aag gct tca ggt tca aga act agt aaa aaa caa gta gag       192
Val Ile Val Lys Ala Ser Gly Ser Arg Thr Ser Lys Lys Gln Val Glu
 50                  55                  60 ata aca tat aat cct gaa gag aag ttt aat aaa tta gct gat gaa gtg       240
Ile Thr Tyr Asn Pro Glu Glu Lys Phe Asn Lys Leu Ala Asp Glu Val
 65                  70                  75                  80 gat aga gaa gct ggg ctt tca aga ctc act ctt ttt tct cct tgc aag       288
Asp Arg Glu Ala Gly Leu Ser Arg Leu Thr Leu Phe Ser Pro Cys Lys
                     85                  90                  95 ata aat gtt ttc ttg aga ata aca agc aag agg gat gac gga tat cat       336
Ile Asn Val Phe Leu Arg Ile Thr Ser Lys Arg Asp Asp Gly Tyr His
                    100                 105                 110 gat ttg gcg tct ctc ttt cat gta att agt cta gga gat aaa ata aag       384
Asp Leu Ala Ser Leu Phe His Val Ile Ser Leu Gly Asp Lys Ile Lys
                    115                 120                 125 ttc tcg ctg tca cca tcg aag tca aag gat cgt tta tct act aat gtt       432
Phe Ser Leu Ser Pro Ser Lys Ser Lys Asp Arg Leu Ser Thr Asn Val
            130                 135                 140 gct gga gtt cca ctc gat gag aga aat ctg att ata aag gcc ctc aat       480
Ala Gly Val Pro Leu Asp Glu Arg Asn Leu Ile Ile Lys Ala Leu Asn
145                 150                 155                 160 ctt tat agg aaa aag act gga aca gac aat tac ttt tgg att cat ctt       528
Leu Tyr Arg Lys Lys Thr Gly Thr Asp Asn Tyr Phe Trp Ile His Leu
                    165                 170                 175 gat aag aaa gtg cct act gga gct ggt ctt ggt ggt ggg agc agt aat       576
Asp Lys Lys Val Pro Thr Gly Ala Gly Leu Gly Gly Gly Ser Ser Asn
                    180                 185                 190 gct gca aca act ctg tgg gca gca aat caa ttc agt ggt tgt gtt gcc       624
Ala Ala Thr Thr Leu Trp Ala Ala Asn Gln Phe Ser Gly Cys Val Ala
                    195                 200                 205 act gaa aag gag ctc caa gag tgg tct ggt gag att ggt tct gat att       672
Thr Glu Lys Glu Leu Gln Glu Trp Ser Gly Glu Ile Gly Ser Asp Ile
210                 215                 220 cct ttc ttc ttc tct cat gga gca gcc tac tgt acg ggt agg ggt gag       720
Pro Phe Phe Phe Ser His Gly Ala Ala Tyr Cys Thr Gly Arg Gly Glu
225                 230                 235                 240 gtt gtt cag gat atc ccg tca ccc ata cca ttt gac att cca atg gtc       768
Val Val Gln Asp Ile Pro Ser Pro Ile Pro Phe Asp Ile Pro Met Val
                    245                 250                 255 ctc ata aag cct caa cag gca tgc tcc act gct gaa gtt tac aag cgt       816
Leu Ile Lys Pro Gln Gln Ala Cys Ser Thr Ala Glu Val Tyr Lys Arg
                    260                 265                 270 ttt cag ttg gat ctg tct agt aag gtt gat ccc ttg agc tta ctg gag       864
Phe Gln Leu Asp Leu Ser Ser Lys Val Asp Pro Leu Ser Leu Leu Glu
                    275                 280                 285 aaa atc tca act agt gga ata tct caa gat gtg tgt gtc aat gat tta       912
Lys Ile Ser Thr Ser Gly Ile Ser Gln Asp Val Cys Val Asn Asp Leu
290                 295                 300 gaa cct cct gcc ttt gaa gtt ctt cca tct ctt aaa agg tta aaa caa       960
Glu Pro Pro Ala Phe Glu Val Leu Pro Ser Leu Lys Arg Leu Lys Gln
305                 310                 315                 320 cga gta att gct gct ggc cga gga caa tat gat gca gtc ttc atg tct      1008
Arg Val Ile Ala Ala Gly Arg Gly Gln Tyr Asp Ala Val Phe Met Ser
                    325                 330                 335 gga agt gga agc aca ata gta ggg gtt ggc tct cca gat cca cca caa      1056
Gly Ser Gly Ser Thr Ile Val Gly Val Gly Ser Pro Asp Pro Pro Gln
                    340                 345                 350
```

-continued

| | | | | | | | | | | | | |
|---|---|---|---|---|---|---|---|---|---|---|---|---|
| ttt | gtc | tat | gat | gat | gaa | gaa | tac | aag | gat | gtc | ttc | ttg | tca | gaa | gca | 1104 |
| Phe | Val | Tyr | Asp | Asp | Glu | Glu | Tyr | Lys | Asp | Val | Phe | Leu | Ser | Glu | Ala | |
| | | 355 | | | | 360 | | | | | 365 | | | | | |
| agt | ttc | atc | act | cga | cca | gcc | aac | gag | tgg | tat | gtt | gaa | cct | gtt | tca | 1152 |
| Ser | Phe | Ile | Thr | Arg | Pro | Ala | Asn | Glu | Trp | Tyr | Val | Glu | Pro | Val | Ser | |
| | 370 | | | | | 375 | | | | | 380 | | | | | |
| ggt | agc | act | att | ggt | gat | caa | cct | gag | ttc | tct | aca | tct | ttt | gac | atg | 1200 |
| Gly | Ser | Thr | Ile | Gly | Asp | Gln | Pro | Glu | Phe | Ser | Thr | Ser | Phe | Asp | Met | |
| 385 | | | | | 390 | | | | | 395 | | | | | 400 | |
| tct | | | | | | | | | | | | | | | | 1203 |
| Ser | | | | | | | | | | | | | | | | |

<210> SEQ ID NO 10
<211> LENGTH: 401
<212> TYPE: PRT
<213> ORGANISM: Lycopersicon esculentum

<400> SEQUENCE: 10

```
Leu Trp Leu Pro Val Ile Phe Val Val Ser Asn Pro Lys Leu Ile
  1               5                  10                  15

Leu Leu Lys Arg Val Val Phe Gln Ser Trp Ser Asn Arg Pro His
             20                  25                  30

Gly Ser Ser Tyr Phe Asn Lys Asn Ile Gln Phe Arg Arg Asn Ser Phe
         35                  40                  45

Val Ile Val Lys Ala Ser Gly Ser Arg Thr Ser Lys Lys Gln Val Glu
 50                  55                  60

Ile Thr Tyr Asn Pro Glu Lys Phe Asn Lys Leu Ala Asp Glu Val
 65                  70                  75                  80

Asp Arg Glu Ala Gly Leu Ser Arg Leu Thr Leu Phe Ser Pro Cys Lys
                 85                  90                  95

Ile Asn Val Phe Leu Arg Ile Thr Ser Lys Arg Asp Asp Gly Tyr His
                100                 105                 110

Asp Leu Ala Ser Leu Phe His Val Ile Ser Leu Gly Asp Lys Ile Lys
            115                 120                 125

Phe Ser Leu Ser Pro Ser Lys Ser Lys Asp Arg Leu Ser Thr Asn Val
    130                 135                 140

Ala Gly Val Pro Leu Asp Glu Arg Asn Leu Ile Ile Lys Ala Leu Asn
145                 150                 155                 160

Leu Tyr Arg Lys Lys Thr Gly Thr Asp Asn Tyr Phe Trp Ile His Leu
                165                 170                 175

Asp Lys Lys Val Pro Thr Gly Ala Gly Leu Gly Gly Ser Ser Asn
            180                 185                 190

Ala Ala Thr Thr Leu Trp Ala Ala Asn Gln Phe Ser Gly Cys Val Ala
        195                 200                 205

Thr Glu Lys Glu Leu Gln Glu Trp Ser Gly Glu Ile Gly Ser Asp Ile
    210                 215                 220

Pro Phe Phe Phe Ser His Gly Ala Ala Tyr Cys Thr Gly Arg Gly Glu
225                 230                 235                 240

Val Val Gln Asp Ile Pro Ser Pro Ile Pro Phe Asp Ile Pro Met Val
                245                 250                 255

Leu Ile Lys Pro Gln Gln Ala Cys Ser Thr Ala Glu Val Tyr Lys Arg
            260                 265                 270

Phe Gln Leu Asp Leu Ser Ser Lys Val Asp Pro Leu Ser Leu Leu Glu
        275                 280                 285

Lys Ile Ser Thr Ser Gly Ile Ser Gln Asp Val Cys Val Asn Asp Leu
    290                 295                 300
```

```
Glu Pro Pro Ala Phe Glu Val Leu Pro Ser Leu Lys Arg Leu Lys Gln
305                 310                 315                 320

Arg Val Ile Ala Ala Gly Arg Gly Gln Tyr Asp Ala Val Phe Met Ser
            325                 330                 335

Gly Ser Gly Ser Thr Ile Val Gly Val Gly Ser Pro Asp Pro Pro Gln
            340                 345                 350

Phe Val Tyr Asp Asp Glu Glu Tyr Lys Asp Val Phe Leu Ser Glu Ala
            355                 360                 365

Ser Phe Ile Thr Arg Pro Ala Asn Glu Trp Tyr Val Glu Pro Val Ser
    370                 375                 380

Gly Ser Thr Ile Gly Asp Gln Pro Glu Phe Ser Thr Ser Phe Asp Met
385                 390                 395                 400

Ser
```

<210> SEQ ID NO 11
<211> LENGTH: 1149
<212> TYPE: DNA
<213> ORGANISM: Arabidopsis thaliana
<220> FEATURE:
<221> NAME/KEY: CDS
<222> LOCATION: (1)..(1149)

<400> SEQUENCE: 11

```
atg gca acg gct tct cct cca ttt atc tca act ctc agc ttc act cac      48
Met Ala Thr Ala Ser Pro Pro Phe Ile Ser Thr Leu Ser Phe Thr His
1               5                   10                  15 tct tct ttc aaa act tct tct tct tct tca ttt tct ccg aag ctt ctt      96
Ser Ser Phe Lys Thr Ser Ser Ser Ser Ser Phe Ser Pro Lys Leu Leu
            20                  25                  30 cga ccc ctc tta agc ttt tcc gtc aaa gct tcc aga aag caa gta gag     144
Arg Pro Leu Leu Ser Phe Ser Val Lys Ala Ser Arg Lys Gln Val Glu
        35                  40                  45 ata gtg ttt gat cct gat gag agg ctt aat aag ata ggt gat gat gtt     192
Ile Val Phe Asp Pro Asp Glu Arg Leu Asn Lys Ile Gly Asp Asp Val
    50                  55                  60 gac aaa gaa gct cct ttg tcc agg ctt aag ctc ttc tca cct tgc aag     240
Asp Lys Glu Ala Pro Leu Ser Arg Leu Lys Leu Phe Ser Pro Cys Lys
65                  70                  75                  80 atc aat gtt ttc ttg agg atc acc gga aag cga gaa gat ggg ttt cat     288
Ile Asn Val Phe Leu Arg Ile Thr Gly Lys Arg Glu Asp Gly Phe His
                85                  90                  95 gat tta gcc tct ttg ttt cat gtg att agc tta gga gac act att aaa     336
Asp Leu Ala Ser Leu Phe His Val Ile Ser Leu Gly Asp Thr Ile Lys
            100                 105                 110 ttc tca ttg tca cca tca aag tct aaa gat cgt ttg tct act aac gtt     384
Phe Ser Leu Ser Pro Ser Lys Ser Lys Asp Arg Leu Ser Thr Asn Val
        115                 120                 125 caa gga gtc cct gtt gat ggg aga aat ctg att ata aaa gca ctt aac     432
Gln Gly Val Pro Val Asp Gly Arg Asn Leu Ile Ile Lys Ala Leu Asn
    130                 135                 140 ctt tac agg aag aaa act ggt agt aac aga ttc ttc tgg att cat tta     480
Leu Tyr Arg Lys Lys Thr Gly Ser Asn Arg Phe Phe Trp Ile His Leu
145                 150                 155                 160 gat aag aag gtg cct acc ggg gct gga ctc ggt ggt gga agt agt aat     528
Asp Lys Lys Val Pro Thr Gly Ala Gly Leu Gly Gly Gly Ser Ser Asn
                165                 170                 175 gct gca act gca ctc tgg gcg gca aat gag ctc aat gga ggt ctt gtc     576
Ala Ala Thr Ala Leu Trp Ala Ala Asn Glu Leu Asn Gly Gly Leu Val
            180                 185                 190
```

-continued

```
act gag aac gaa ctc cag gat tgg tca agt gaa att ggg tca gat att       624
Thr Glu Asn Glu Leu Gln Asp Trp Ser Ser Glu Ile Gly Ser Asp Ile
        195                 200                 205 cct ttc ttc ttc tcg cat gga gct gcc tat tgt acc ggg aga ggt gag       672
Pro Phe Phe Phe Ser His Gly Ala Ala Tyr Cys Thr Gly Arg Gly Glu
    210                 215                 220 att gtc caa gac ctt cct cca cct ttt cct ctt gat ctt ccg atg gtg       720
Ile Val Gln Asp Leu Pro Pro Pro Phe Pro Leu Asp Leu Pro Met Val
225                 230                 235                 240 ctc ata aag ccc cga gaa gca tgt tcc act gct gaa gtt tac aaa cgt       768
Leu Ile Lys Pro Arg Glu Ala Cys Ser Thr Ala Glu Val Tyr Lys Arg
                245                 250                 255 ctt cgt tta gat cag acg agc aat att aat ccc ttg aca tta cta gag       816
Leu Arg Leu Asp Gln Thr Ser Asn Ile Asn Pro Leu Thr Leu Leu Glu
            260                 265                 270 aat gtg acc agc aat ggt gtg tct caa agc ata tgc gta aac gat ttg       864
Asn Val Thr Ser Asn Gly Val Ser Gln Ser Ile Cys Val Asn Asp Leu
        275                 280                 285 gaa ccg cca gcg ttt tca gtt ctt cca tct cta aaa cgc ttg aag caa       912
Glu Pro Pro Ala Phe Ser Val Leu Pro Ser Leu Lys Arg Leu Lys Gln
    290                 295                 300 cgg ata ata gca tct gga cgt ggg gaa tac gat gct gtg ttt atg tct       960
Arg Ile Ile Ala Ser Gly Arg Gly Glu Tyr Asp Ala Val Phe Met Ser
305                 310                 315                 320 ggg agt gga agc act att atc ggt att ggt tca cca gat cct cct caa      1008
Gly Ser Gly Ser Thr Ile Ile Gly Ile Gly Ser Pro Asp Pro Pro Gln
                325                 330                 335 ttt ata tat gat gat gaa gaa tac aag aac gtg ttc ttg tct gaa gca      1056
Phe Ile Tyr Asp Asp Glu Glu Tyr Lys Asn Val Phe Leu Ser Glu Ala
            340                 345                 350 aac ttt atg acg cgt gag gct aat gaa tgg tac aaa gaa cct gct tct      1104
Asn Phe Met Thr Arg Glu Ala Asn Glu Trp Tyr Lys Glu Pro Ala Ser
        355                 360                 365 gca aat gct act acc tca tcc gcc gaa tct cgc atg gat ttc caa          1149
Ala Asn Ala Thr Thr Ser Ser Ala Glu Ser Arg Met Asp Phe Gln
    370                 375                 380
```

<210> SEQ ID NO 12
<211> LENGTH: 383
<212> TYPE: PRT
<213> ORGANISM: Arabidopsis thaliana

<400> SEQUENCE: 12

```
Met Ala Thr Ala Ser Pro Pro Phe Ile Ser Thr Leu Ser Phe Thr His
1               5                  10                  15

Ser Ser Phe Lys Thr Ser Ser Ser Ser Phe Ser Pro Lys Leu Leu
                20                  25                  30

Arg Pro Leu Leu Ser Phe Ser Val Lys Ala Ser Arg Lys Gln Val Glu
            35                  40                  45

Ile Val Phe Asp Pro Asp Glu Arg Leu Asn Lys Ile Gly Asp Asp Val
        50                  55                  60

Asp Lys Glu Ala Pro Leu Ser Arg Leu Lys Leu Phe Ser Pro Cys Lys
65                  70                  75                  80

Ile Asn Val Phe Leu Arg Ile Thr Gly Lys Arg Glu Asp Gly Phe His
                85                  90                  95

Asp Leu Ala Ser Leu Phe His Val Ile Ser Leu Gly Asp Thr Ile Lys
            100                 105                 110

Phe Ser Leu Ser Pro Ser Lys Ser Lys Asp Arg Leu Ser Thr Asn Val
```

```
            115                 120                     125
Gln Gly Val Pro Val Asp Gly Arg Asn Leu Ile Ile Lys Ala Leu Asn
    130                 135                 140

Leu Tyr Arg Lys Lys Thr Gly Ser Asn Arg Phe Phe Trp Ile His Leu
145                 150                     155                 160

Asp Lys Lys Val Pro Thr Gly Ala Gly Leu Gly Gly Ser Ser Asn
                165                 170                 175

Ala Ala Thr Ala Leu Trp Ala Ala Asn Glu Leu Asn Gly Gly Leu Val
            180                 185                 190

Thr Glu Asn Glu Leu Gln Asp Trp Ser Ser Glu Ile Gly Ser Asp Ile
        195                 200                 205

Pro Phe Phe Phe Ser His Gly Ala Ala Tyr Cys Thr Gly Arg Gly Glu
            210                 215                 220

Ile Val Gln Asp Leu Pro Pro Phe Pro Leu Asp Leu Pro Met Val
225                 230                 235                 240

Leu Ile Lys Pro Arg Glu Ala Cys Ser Thr Ala Glu Val Tyr Lys Arg
                245                 250                 255

Leu Arg Leu Asp Gln Thr Ser Asn Ile Asn Pro Leu Thr Leu Leu Glu
            260                 265                 270

Asn Val Thr Ser Asn Gly Val Ser Gln Ser Ile Cys Val Asn Asp Leu
        275                 280                 285

Glu Pro Pro Ala Phe Ser Val Leu Pro Ser Leu Lys Arg Leu Lys Gln
290                 295                 300

Arg Ile Ile Ala Ser Gly Arg Gly Glu Tyr Asp Ala Val Phe Met Ser
305                 310                 315                 320

Gly Ser Gly Ser Thr Ile Ile Gly Ile Gly Ser Pro Asp Pro Pro Gln
                325                 330                 335

Phe Ile Tyr Asp Asp Glu Glu Tyr Lys Asn Val Phe Leu Ser Glu Ala
                340                 345                 350

Asn Phe Met Thr Arg Glu Ala Asn Glu Trp Tyr Lys Glu Pro Ala Ser
            355                 360                 365

Ala Asn Ala Thr Thr Ser Ser Ala Glu Ser Arg Met Asp Phe Gln
    370                 375                 380

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: conserved
      motif
<221> NAME/KEY: PEPTIDE
<222> LOCATION: (1)..(16)
<223> OTHER INFORMATION: glycine-rich conserved motif characteristic of
      preferred isopentenyl monophosphate kinases wherein Xaa
      at positions 2 and 15 represent any amino acid and Xaa
      at position 16 represents lysine or arginine

<400> SEQUENCE: 13

Pro Xaa Gly Ala Gly Leu Gly Gly Gly Ser Ser Asn Ala Ala Xaa Xaa
 1               5                  10                  15

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: conserved
      sequence
<221> NAME/KEY: PEPTIDE
```

```
<222> LOCATION: (1)..(13)
<223> OTHER INFORMATION: conserved sequence domain characteristic of GHMP
      kinases wherein Xaa at positions 2, 3, 4, 11 and 12
      represent any amino acid, Xaa at position 7 represents
      glycine or serine, Xaa at position 10 represents

<400> SEQUENCE: 14

Pro Xaa Xaa Xaa Gly Leu Xaa Ser Ser Xaa Xaa Xaa Xaa
  1               5                  10

<210> SEQ ID NO 15
<211> LENGTH: 945
<212> TYPE: DNA
<213> ORGANISM: Synechocystis sp.
<220> FEATURE:
<221> NAME/KEY: CDS
<222> LOCATION: (1)..(945)

<400> SEQUENCE: 15
```

| | | | | | | | | | | | | | | | | |
|---|---|---|---|---|---|---|---|---|---|---|---|---|---|---|---|---|
| atg | cat | tcc | tac | acc | ctc | cat | gcc | ccg | gcc | aaa | att | aat | ctt | ttc | ctc | 48 |
| Met | His | Ser | Tyr | Thr | Leu | His | Ala | Pro | Ala | Lys | Ile | Asn | Leu | Phe | Leu | |
| 1 | | | | 5 | | | | | 10 | | | | | 15 | | |
| gaa | att | ctt | ggc | gat | cgc | ccc | gac | ggt | ttc | cac | gaa | ttg | gta | atg | gtg | 96 |
| Glu | Ile | Leu | Gly | Asp | Arg | Pro | Asp | Gly | Phe | His | Glu | Leu | Val | Met | Val | |
| | | | 20 | | | | | 25 | | | | | 30 | | | |
| ttg | cag | agc | att | gcc | ctg | ggg | gat | aaa | att | acc | gtg | cgg | gcc | aac | ggc | 144 |
| Leu | Gln | Ser | Ile | Ala | Leu | Gly | Asp | Lys | Ile | Thr | Val | Arg | Ala | Asn | Gly | |
| | 35 | | | | | 40 | | | | | 45 | | | | | |
| acc | gat | gac | atc | cgg | ctc | agt | tgt | ggg | gat | agt | ccc | ttg | gcc | aac | gat | 192 |
| Thr | Asp | Asp | Ile | Arg | Leu | Ser | Cys | Gly | Asp | Ser | Pro | Leu | Ala | Asn | Asp | |
| 50 | | | | | 55 | | | | | 60 | | | | | | |
| gcc | acc | aat | ttg | gcc | tac | cga | gcg | gcc | cag | ttg | atg | att | aac | aat | ttt | 240 |
| Ala | Thr | Asn | Leu | Ala | Tyr | Arg | Ala | Ala | Gln | Leu | Met | Ile | Asn | Asn | Phe | |
| 65 | | | | | 70 | | | | | 75 | | | | | 80 | |
| ccc | caa | gcc | cat | gat | aat | tac | ggc | ggc | gta | gat | atc | acc | ttg | acc | aag | 288 |
| Pro | Gln | Ala | His | Asp | Asn | Tyr | Gly | Gly | Val | Asp | Ile | Thr | Leu | Thr | Lys | |
| | | | | 85 | | | | | 90 | | | | | 95 | | |
| cat | att | ccc | atg | gcg | gcg | ggc | tta | gcg | ggg | ggc | tcg | gcc | gat | gca | gcg | 336 |
| His | Ile | Pro | Met | Ala | Ala | Gly | Leu | Ala | Gly | Gly | Ser | Ala | Asp | Ala | Ala | |
| | | | 100 | | | | | 105 | | | | | 110 | | | |
| gcg | gtg | tta | gtc | ggt | tta | gac | ctg | ctc | tgg | aat | tta | ggc | tta | acc | agg | 384 |
| Ala | Val | Leu | Val | Gly | Leu | Asp | Leu | Leu | Trp | Asn | Leu | Gly | Leu | Thr | Arg | |
| | 115 | | | | | 120 | | | | | 125 | | | | | |
| ccg | gaa | tta | gaa | cag | tta | gcg | gcc | caa | ctg | ggt | tcc | gac | att | ccc | ttt | 432 |
| Pro | Glu | Leu | Glu | Gln | Leu | Ala | Ala | Gln | Leu | Gly | Ser | Asp | Ile | Pro | Phe | |
| 130 | | | | | 135 | | | | | 140 | | | | | | |
| tgc | att | ggc | ggt | ggc | acg | gcg | atc | gcc | acg | gga | cgg | ggg | gaa | atc | ctc | 480 |
| Cys | Ile | Gly | Gly | Gly | Thr | Ala | Ile | Ala | Thr | Gly | Arg | Gly | Glu | Ile | Leu | |
| 145 | | | | | 150 | | | | | 155 | | | | | 160 | |
| gac | ccc | tta | ccg | gac | ggc | aat | tgc | ttc | tgg | gtg | gta | ttg | gcc | aaa | cat | 528 |
| Asp | Pro | Leu | Pro | Asp | Gly | Asn | Cys | Phe | Trp | Val | Val | Leu | Ala | Lys | His | |
| | | | | 165 | | | | | 170 | | | | | 175 | | |
| cgt | tcc | ata | gaa | gtt | tct | acc | ccc | tgg | gct | tac | caa | acc | tat | cgt | caa | 576 |
| Arg | Ser | Ile | Glu | Val | Ser | Thr | Pro | Trp | Ala | Tyr | Gln | Thr | Tyr | Arg | Gln | |
| | | | 180 | | | | | 185 | | | | | 190 | | | |
| aag | ttt | ggc | aag | aat | tac | cta | aac | gat | gac | cag | tcc | cag | cga | gcc | cgg | 624 |
| Lys | Phe | Gly | Lys | Asn | Tyr | Leu | Asn | Asp | Asp | Gln | Ser | Gln | Arg | Ala | Arg | |
| | 195 | | | | | 200 | | | | | 205 | | | | | |
| cgg | aaa | acc | atc | cat | gca | ggg | ccc | cta | ctc | cag | ggc | att | cag | cac | cgc | 672 |
| Arg | Lys | Thr | Ile | His | Ala | Gly | Pro | Leu | Leu | Gln | Gly | Ile | Gln | His | Arg | |
| 210 | | | | | 215 | | | | | 220 | | | | | | |
| aac | cca | ggg | caa | atc | gcc | agc | cat | atc | cac | aac | gat | tta | gaa | aaa | gtt | 720 |

-continued

```
Asn Pro Gly Gln Ile Ala Ser His Ile His Asn Asp Leu Glu Lys Val
225                 230                 235                 240 gtg ctc ccg gct cat cag cct gta gcc cag tta cgt cag gtc cta cag        768
Val Leu Pro Ala His Gln Pro Val Ala Gln Leu Arg Gln Val Leu Gln
                245                 250                 255 tca gcg ggg gga ttg ggc acc atg atg tcc ggc tcc ggc ccc agc gtg        816
Ser Ala Gly Gly Leu Gly Thr Met Met Ser Gly Ser Gly Pro Ser Val
            260                 265                 270 ttt acc ctt tgc cgg gag caa gca gaa gcg gaa cag gtc ctg gcg atc        864
Phe Thr Leu Cys Arg Glu Gln Ala Glu Ala Glu Gln Val Leu Ala Ile
        275                 280                 285 gcc aaa gaa aaa tta aac gac ccc gac gtg gat ttt tgg cta acc cac        912
Ala Lys Glu Lys Leu Asn Asp Pro Asp Val Asp Phe Trp Leu Thr His
    290                 295                 300 acc atc ggc cac ggc atc caa att atg aat aat                            945
Thr Ile Gly His Gly Ile Gln Ile Met Asn Asn
305                 310                 315
```

<210> SEQ ID NO 16
<211> LENGTH: 315
<212> TYPE: PRT
<213> ORGANISM: Synechocystis sp.

<400> SEQUENCE: 16

```
Met His Ser Tyr Thr Leu His Ala Pro Ala Lys Ile Asn Leu Phe Leu
 1               5                  10                  15

Glu Ile Leu Gly Asp Arg Pro Asp Gly Phe His Glu Leu Val Met Val
                20                  25                  30

Leu Gln Ser Ile Ala Leu Gly Asp Lys Ile Thr Val Arg Ala Asn Gly
            35                  40                  45

Thr Asp Asp Ile Arg Leu Ser Cys Gly Asp Ser Pro Leu Ala Asn Asp
        50                  55                  60

Ala Thr Asn Leu Ala Tyr Arg Ala Ala Gln Leu Met Ile Asn Asn Phe
    65                  70                  75                  80

Pro Gln Ala His Asp Asn Tyr Gly Gly Val Asp Ile Thr Leu Thr Lys
                85                  90                  95

His Ile Pro Met Ala Ala Gly Leu Ala Gly Gly Ser Ala Asp Ala Ala
            100                 105                 110

Ala Val Leu Val Gly Leu Asp Leu Leu Trp Asn Leu Gly Leu Thr Arg
        115                 120                 125

Pro Glu Leu Glu Gln Leu Ala Ala Gln Leu Gly Ser Asp Ile Pro Phe
    130                 135                 140

Cys Ile Gly Gly Gly Thr Ala Ile Ala Thr Gly Arg Gly Glu Ile Leu
145                 150                 155                 160

Asp Pro Leu Pro Asp Gly Asn Cys Phe Trp Val Val Leu Ala Lys His
                165                 170                 175

Arg Ser Ile Glu Val Ser Thr Pro Trp Ala Tyr Gln Thr Tyr Arg Gln
            180                 185                 190

Lys Phe Gly Lys Asn Tyr Leu Asn Asp Asp Gln Ser Gln Arg Ala Arg
        195                 200                 205

Arg Lys Thr Ile His Ala Gly Pro Leu Leu Gln Gly Ile Gln His Arg
    210                 215                 220

Asn Pro Gly Gln Ile Ala Ser His Ile His Asn Asp Leu Glu Lys Val
225                 230                 235                 240

Val Leu Pro Ala His Gln Pro Val Ala Gln Leu Arg Gln Val Leu Gln
                245                 250                 255
```

-continued

```
Ser Ala Gly Gly Leu Gly Thr Met Met Ser Gly Ser Gly Pro Ser Val
            260                 265                 270

Phe Thr Leu Cys Arg Glu Gln Ala Glu Ala Glu Gln Val Leu Ala Ile
            275                 280                 285

Ala Lys Glu Lys Leu Asn Asp Pro Asp Val Asp Phe Trp Leu Thr His
    290                 295                 300

Thr Ile Gly His Gly Ile Gln Ile Met Asn Asn
305                 310                 315
```

NUCLEIC ACID MOLECULES ENCODING ISOPENTENYL MONOPHOSPHATE KINASE, AND METHODS OF USE

GOVERNMENT RIGHTS

This invention was funded in part by United States Department of Energy grant number DE-FG03-96ER20212. The government has certain rights in this invention.

FIELD OF THE INVENTION

This invention relates to nucleic acid sequences encoding isopentenyl monophosphate kinase, in particular to nucleic acid sequences encoding isopentenyl monophosphate kinase from peppermint.

BACKGROUND OF THE INVENTION

Isopentenyl diphosphate (IPP) is the central intermediate in the biosynthesis of isoprenoids in all organisms. In higher plants, the formation of IPP is compartmentalized. The mevalonate (MVA) pathway, the enzymes of which are localized to the cytosolic compartment, produces the precursor of triterpenes (sterols) and certain sesquiterpenes (Newman, J. D. & Chappell, J., *Crit. Rev. Biochem. Mol. Biol.*, 34:95–106 [1999]). In plastids, the deoxyxylulose-5-phosphate (DXP) pathway operates to supply IPP for the synthesis of monoterpenes and diterpenes (Eisenreich, W. et al., *Tetrahedron Lett.*, 38:3889–3892 [1997]; Eisenreich, W. et al., *Proc. Natl. Acad. Sci. USA*, 93:6431–6436 [1996]), several sequiterpenes (McCaskill, D. & Croteau, R., *Planta*, 197:49–56 [1995]), tetraterpenes (carotenoids), and the prenyl side-chains of chlorophyll and plastoquinone (Lichtenthaler, H. K. et al., *FEBS Lett.*, 400:271–274 [1997]).

In addition, there are examples of cooperation between the cytosolic and plastidial pathways in the biosynthesis of stress-induced and constitutively emitted volatile terpenoids from a variety of plants (Piel, J. et al., *Angew. Chem. Int. Ed.*, 37:2478–2481 [1998]), and constitutive sesquiterpenes of chamomile (Adam, K.-P. & Zapp, J., *Phytochemistry*, 48:953–959 [1998]). In mammals, where the DXP pathway is not known to operate, and in plants, the individual biosynthetic steps of the MVA pathway have been well-characterized (Goldstein, J. L. & Brown, M. S., *Nature (London)*, 343:425–430 [1990]; Bach, T. J., *Crit. Rev. Biochem. Mol. Biol.*, 34:107–122 [1999]). However, for the recently discovered DXP pathway, which also occurs in many eubacteria (Rohmer, M., *Prog. Drug Res.*, 50:135–154 [1998]), the biosynthetic sequence leading to the formation of IPP is still incompletely defined (The FIGURE).

The initial step of the pathway involves a condensation of pyruvate (C2 and C3) with D-glyceraldehyde-3-phosphate (GAP) to yield 1-deoxy-D-xylulose-5-phosphate (Rohmer, M., *Biochem. J.*, 295:517–524 [1993]; Broers, S. T. J., Ph.D. thesis, Eidgenössische Technische Hochschule, Zürich, Switzerland [1994]; Schwarz, M. K., Ph.D. thesis, Eidgenössische Technische Hochschule, Zürich, Switzerland [1994]; Rohmer, M. et al., *J. Am. Chem. Soc.*, 118:2564–2566 [1996]). The enzyme which catalyzes this reaction belongs to a novel family of transketolases, and the corresponding gene has been isolated from *Escherichia coli* (Sprenger, G. A. et al., *Proc. Natl. Acad. Sci. USA*, 94:12857–12862 [1997]; Lois, L. M. et al., *Proc. Natl. Acad. Sci. USA*, 95:2105–2110 [1997]), peppermint (Lange, B. M. et al., *Proc. Natl. Acad. Sci. USA*, 95:2100–2104 [1998]) and pepper (Bouvier, F. et al., *Plant Physiol.*, 117:1423–1431 [1998]). In the second step of this pathway, rearrangement and reduction of DXP yield 2-C-methyl-D-erythritol (MEP) (Duvold, T. et al., *Tetrahedron Lett.*, 38:4769–4772 [1997]; Duvold, T. et al., *Tetrahedron Lett.*, 38:6181–6184 [1997]; Sagner, S. et al., *Tetrahedron Lett.*, 39:2091–2094 [1998]) (The FIGURE). Recently, genes encoding this DXP reductoisomerase (DXR) have been cloned from *E. coli* (Takahashi, S. et al., *Proc. Natl. Acad. Sci. USA*, 95:9879–9884 [1998]), peppermint (Lange, B. M. & Croteau R., *Arch. Biochem. Biophys.*, 365:170–174 [1999]), and *Arabidopsis thaliana* (Lange, B. M. & Croteau R., *Arch. Biochem. Biophys.*, 365:170–174 [1999]; Schwender, J. et al., *FEBS Lett.*, 455:140–144 [1999]). To date, no other intermediates on the route to IPP, the terminal product of the DXP pathway (McCaskill, D. & Croteau R., *Tetrahedron Lett.*, 40:653–656 [1999]; Arigoni, D. et al., *Proc. Natl. Acad. Sci. USA*, 96:1309–1314 [1999]), have been identified.

As disclosed herein, sequencing of 1300 anonymous clones (expressed sequence tags, ESTs) from a cDNA library constructed from mRNA isolated from the oil gland secretory cells of peppermint (*Mentha x piperita*) (McCaskill, D. & Croteau, R., *Planta*, 197:49–56 [1995]), afforded, after extensive database comparisons, two clones having homologues of unknown function in plants and eubacteria, the sequences of which contained a motif with homology to the putative ATP-binding domain of the GHMP (galactokinase, homoserine kinase, mevalonate kinase, and phosphomevalonate kinase) family of metabolite kinases. This putative kinase gene from peppermint and its *E. coli* orthologue, when overexpressed in *E. coli*, yielded a recombinant enzyme that catalyzes the ATP-dependent phosphorylation of isopentenol monophosphate (IP) to IPP. Feeding experiments with IP and several other isoprenoid precursors, using isolated peppermint secretory cells, confirmed the phosphorylation of IP to IPP to be the last step in the DXP pathway.

SUMMARY OF THE INVENTION

In accordance with the foregoing, a cDNA encoding isopentenyl monophosphate kinase (IPK) from peppermint (*Mentha x piperita*) has been isolated and sequenced, and the corresponding amino acid sequence has been deduced. Accordingly, the present invention relates to isolated DNA sequences which code for the expression of isopentenyl monophosphate kinase, such as the sequence designated SEQ ID NO:1 which encodes an isopentenyl monophosphate kinase protein (SEQ ID NO:2) from peppermint (*Mentha x piperita*). Additionally, the present invention relates to isolated, recombinant isopentenyl monophosphate kinase proteins, such as the isolated, recombinant isopentenyl monophosphate kinase protein from peppermint (*Mentha x piperita*) (SEQ ID NO:2). In other aspects, the present invention is directed to replicable recombinant cloning vehicles comprising a nucleic acid sequence, e.g., a DNA sequence which codes for an isopentenyl monophosphate kinase, or for a base sequence sufficiently complementary to at least a portion of DNA or RNA encoding isopentenyl monophosphate kinase to enable hybridization therewith (e.g., antisense RNA or fragments of DNA complementary to a portion of DNA or RNA molecules encoding isopentenyl monophosphate kinase which are useful as polymerase chain reaction primers or as probes for isopentenyl monophosphate kinase or related genes). In yet other aspects of the invention, modified host cells are provided that have been transformed, transfected, infected and/or injected with a recombinant cloning vehicle and/or DNA sequence of the invention. Thus, the present invention provides for the recombinant expression of isopentenyl monophosphate kinase, and the inventive concepts may be used to facilitate the production, isolation and purification of significant quantities of recombinant isopentenyl monophosphate kinase (or of its primary enzyme products) for subsequent use, to obtain expression or enhanced expression of isopentenyl monophosphate kinase in plants, microorganisms or animals, or may be otherwise employed in an environment where the regulation or expression of isopentenyl monophosphate kinase is desired for the production of this kinase, or its enzyme product, or derivatives thereof.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

The FIGURE shows the DXP pathway for the biosynthesis of IPP, and the proposed role of IPK. The circled P denotes the phosphate moiety. The large open arrow indicates several as yet unidentified steps.

DETAILED DESCRIPTION OF THE PREFERRED EMBODIMENT

As used herein, the terms "amino acid" and "amino acids" refer to all naturally occurring L-α-amino acids or their residues. The amino acids are identified by either the single-letter or three-letter designations:

| Asp | D | aspartic acid |
| Thr | T | threonine |
| Ser | S | serine |
| Glu | E | glutamic acid |
| Pro | P | proline |
| Gly | G | glycine |
| Ala | A | alanine |
| Cys | C | cysteine |
| Val | V | valine |
| Met | M | methionine |
| Ile | I | isoleucine |
| Leu | L | leucine |
| Tyr | Y | tyrosine |
| Phe | F | phenylalanine |
| His | H | histidine |
| Lys | K | lysine |
| Arg | R | arginine |
| Trp | W | tryptophan |
| Gln | Q | glutamine |
| Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A,G,C and uracil ("U"). The nucleotide sequences described herein comprise a linear array of nucleotides connected by phosphodiester bonds between the 3' and 5' carbons of adjacent pentoses.

Abbreviations used herein include: DMA, dimethylallyl alcohol; DMAP, dimethylallyl monophosphate; DMAPP, dimethylallyl diphosphate; DX, deoxyxylulose; DXP, deoxyxylulose-5-phosphate; DXPS, 1-deoxyxylulose-5-phosphate synthase; DXR, deoxyxylulose-5-phosphate reductoisomerase; EST, expressed sequence tag; GAP, glyceraldehyde-3-phosphate; IP, isopentenyl monophosphate; IPK, isopentenyl monophosphate kinase; IPP, isopentenyl diphosphate; ISO, isopentenol; MEP, 2-C-methylerythritol-4-phosphate; MVA, mevalonate; PCR, polymerase chain reaction.

The term "percent identity" (% I) means the percentage of amino acids or nucleotides that occupy the same relative position when two amino acid sequences, or two nucleic acid sequences, are aligned side by side.

The term "percent similarity" (% S) is a statistical measure of the degree of relatedness of two compared protein sequences. The percent similarity is calculated by a computer program that assigns a numerical value to each compared pair of amino acids based on observed amino acid replacements in closely related sequences. Calculations are made after a best fit alignment of the two sequences has been made empirically by iterative comparison of all possible alignments. (Henikoff, S. and Henikoff, J. G., Proc. Nat'l Acad Sci USA 89:10915–10919 [1992]).

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "isopentenyl monophosphate kinase" is used herein to mean an enzyme capable of catalyzing the ATP-dependent phosphorylation of isopentenol monophosphate (IP) to isopentenyl diphosphate IPP.

The term "essential oil plant," or "essential oil plants," refers to a group of plant species that produce high levels of monoterpenoid and/or sesquiterpenoid and/or diterpenoid oils, and/or high levels of monoterpenoid and/or sesquiterpenoid and/or diterpenoid resins. The foregoing oils and/or resins account for greater than about 0.005% of the fresh weight of an essential oil plant that produces them. The essential oils and/or resins are more fully described, for example, in E. Guenther, The Essential Oils, Vols. I–VI, R. E. Krieger Publishing Co., Huntington N.Y., 1975, incorporated herein by reference. The essential oil plants include, but are not limited to:

Lamiaceae, including, but not limited to, the following species: Ocimum (basil), Lavandula (Lavender), Origanum (oregano), Mentha (mint), Salvia (sage), Rosmarinus (rosemary), Thymus (thyme), Satureja and Monarda.

Umbelliferae, including, but not limited to, the following species: Carum (caraway), Anethum (dill), feniculum (fennel) and Daucus (carrot).

Asteraceae (Compositae), including, but not limited to, the following species: Artemisia (tarragon, sage brush), Tanacetum (tansy).

Rutaceae (e.g., citrus plants); Rosaceae (e.g., roses); Myrtaceae (e.g., eucalyptus, Melaleuca); the Gramineae (e.g., Cymbopogon (citronella)); Geranaceae (Geranium) and certain conifers including Abies (e.g., Canadian balsam), Cedrus (cedar), Thuja, Pinus (pines) and Juniperus.

The range of essential oil plants is more fully set forth in E. Guenther, The Essential Oils, Vols. I–VI, R. E. Krieger Publishing Co., Huntington N.Y., 1975, which is incorporated herein by reference.

The term "angiosperm" refers to a class of plants that produce seeds that are enclosed in an ovary.

The term "gymnosperm" refers to a class of plants that produce seeds that are not enclosed in an ovary.

The terms "alteration", "amino acid sequence alteration", "variant" and "amino acid sequence variant" refer to isopentenyl monophosphate kinase molecules with some differences in their amino acid sequences as compared to native isopentenyl monophosphate kinase. Ordinarily, the variants will possess at least about 70% homology with native isopentenyl monophosphate kinase, and preferably they will be at least about 80% homologous with native isopentenyl monophosphate kinase. The amino acid sequence variants of isopentenyl monophosphate kinase falling within this invention possess substitutions, deletions, and/or insertions at certain positions. Sequence variants of isopentenyl monophosphate kinase may be used to attain desired enhanced or reduced enzymatic activity, or altered substrate utilization or product distribution of isopentenyl monophosphate kinase.

Substitutional isopentenyl monophosphate kinase variants are those that have at least one amino acid residue in the native isopentenyl monophosphate kinase sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the isopentenyl monophosphate kinase molecule may be obtained by substituting an amino acid with a side chain that is significantly different in charge and/or structure from that of the native amino acid. This type of substitution would be expected to affect the structure of the polypeptide backbone and/or the charge or hydrophobicity of the molecule in the area of the substitution.

Moderate changes in the activity of the isopentenyl monophosphate kinase molecule would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution.

Insertional isopentenyl monophosphate kinase variants are those with one or more amino acids inserted immediately adjacent to an amino acid at a particular position in the native isopentenyl monophosphate kinase molecule. Immediately adjacent to an amino acid means connected to either the α-carboxy or α-amino functional group of the amino acid. The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native isopentenyl monophosphate kinase molecule have been removed. Ordinarily, deletional variants will have one or two amino acids deleted in a particular region of the isopentenyl monophosphate kinase molecule.

The terms "biological activity", "biologically active", "activity" and "active," when used with reference to isopentenyl monophosphate kinase, refer to the ability of isopentenyl monophosphate kinase to catalyze the ATP-dependent phosphorylation of isopentenol monophosphate (IP) to isopentenyl diphosphate IPP, as measured in an enzyme activity assay, such as the assay described in Example 1 below. Amino acid sequence variants of isopentenyl monophosphate kinase may have desirable, altered biological activity including, for example, altered reaction kinetics, substrate utilization product distribution or other characteristics.

The terms "DNA sequence encoding", "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The terms "replicable expression vector" and "expression vector" refer to a piece of DNA, usually double-stranded, which may have inserted into it a piece of DNA called the insert DNA, which is usually foreign DNA. Foreign DNA is defined as heterologous DNA, which is DNA not naturally found in the host. The vector is used to transport the insert DNA into a suitable host cell. Once in the host cell, the vector can replicate independently of or coincidental with the host chromosomal DNA, and several copies of the vector and its inserted DNA may be generated. In addition, the vector contains the necessary elements that permit translating the insert DNA into a polypeptide. Many molecules of the polypeptide encoded by the insert DNA can thus be rapidly synthesized.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In accordance with the present invention, a cDNA encoding isopentenyl monophosphate kinase was isolated and sequenced in the following manner. A λZAP cDNA library was constructed from mRNA obtained from isolated peppermint oil gland secretory cells. Randomly picked and purified clones were excised in vivo and inserts of the resulting phagemids were partially sequenced. An apparently full-length IP kinase clone (designated ml100) (SEQ ID NO:1) was acquired by this means and was used as a template to amplify by PCR a 1218 base pair fragment (corresponding to nucleic acid residues 3–1217 of SEQ ID NO:1) using the primers 5'-ATGGCTTCCTCCT-CCCATTTCCTC-3' (forward) (SEQ ID NO:3) and 5'-TTCAGCATCCTGAGGAAAAGACGG-3' (reverse) (SEQ ID NO:4), which was subsequently cloned into the expression vector pBAD TOPO TA (Invitrogen). Clone ml100 (SEQ ID NO:1) shared a region of high sequence similarity to the putative ATP-binding domain of the GHMP family of kinases. The expressed enzyme strongly tended to form inclusion bodies, and soluble protein could not be obtained in sufficient quantity for affinity-based purification. Thus, crude extracts of sonicated, transformed cells served as the enzyme source for kinase assays. Consistently, the expressed recombinant peppermint kinase gave detectably elevated levels of activity with isopentenol monophosphate and isopentenol as substrates, when compared to the *E. coli* background. No phosphokinase activity was detected with dimethylallyl monophosphate (DMAP) or MVA as substrate. Kinase activity with dimethyallyl alcohol (DMA) as a substrate, under the standard assay conditions, was always detectable, but never exceeded 0.01 pmol (s g protein)$^{-1}$.

With DXP, deoxylylulose (DX) and MEP as substrates, kinase activity of less than 0.2 pmol (s g protein)$^{-1}$ was occasionally detected but in most experiments no activity was observed.

A putative E. coli IP kinase gene (SEQ ID NO:5), encoding the protein having the amino acid sequence set forth in (SEQ ID NO:6) was amplified by PCR using the primers 5'-ATGCGGACACAGTGGCCCTC-3' (forward) (SEQ ID NO:7) and 5'-AAGCATGGCTCTGTGCAATG-3' (reverse) (SEQ ID NO:8), and genomic DNA from the strain K-12 MG1655 (wild-type) as a template. For expression, the amplicon was cloned into pBAD TOPO TA (Invitrogen) and transformed into E. coli strain TOP10 One Shot. Assay of crude extracts gave results similar to those obtained with the recombinant peppermint enzyme. However, in this instance, the expressed, soluble enzyme, produced upon induction with 0.02% arabinose, allowed a useful one-step affinity-based purification with a Ni$^{2+}$-binding column. This partially purified protein readily catalyzed the conversion of IP to IPP, ISO to IP, and DMA to DMAP; however, no phosphorylating activity was detectable with DMAP, DXP, DX, MEP or MVA as substrate. This kinase activity (with IP as a substrate) was dependent upon the presence of MgCl$_2$ as divalent cation and ATP as phosphate donor, whereas CTP, UTP and GTP did not serve as alternate phosphate donors. These results with the enzyme products of the peppermint ml100 clone (SEQ ID NO:1) and the E. coli ychB clone (SEQ ID NO:5) indicate that this gene (SEQ ID NO:1) encodes an isopentenyl monophosphate kinase (IPK) that is involved in the DXP pathway to isoprenoids.

The isolation of a cDNA encoding isopentenyl monophosphate kinase permits the development of an efficient expression system for this protein, provides a useful tool for examining the developmental regulation of isoprenoid biosynthesis and permits the isolation of other isopentenyl monophosphate kinases. The isolation of an isopentenyl monophosphate kinase cDNA also permits the transformation of a wide range of organisms, for example to modify endogenous isoprenoid biosynthesis.

Although the isopentenyl monophosphate kinase protein set forth in SEQ ID NO:2 directs the enzyme to plastids, substitution of the putative targeting sequence (SEQ ID NO:2, amino acids 1 to 98) with other transport sequences well known in the art (see, e.g., von Heijne G et al., Eur. J. Biochem 180:535–545 [1989]; Stryer, Biochemistry W. H. Freeman and Company, New York, N.Y., p. 769 [1988]) may be employed to direct the isopentenyl monophosphate kinase to other cellular or extracellular locations.

In addition to native isopentenyl monophosphate kinase amino acid sequences, such as the native isopentenyl monophosphate kinase amino acid sequence of SEQ ID NO:2, sequence variants produced by deletions, substitutions, mutations and/or insertions are intended to be within the scope of the invention except insofar as limited by the prior art. Isopentenyl monophosphate kinase amino acid sequence variants may be constructed by mutating the DNA sequence that encodes wild-type isopentenyl monophosphate kinase, such as by using techniques commonly referred to as site-directed mutagenesis. Various polymerase chain reaction (PCR) methods now well known in the field, such as a two primer system like the Transformer Site-Directed Mutagenesis kit from Clontech, may be employed for this purpose.

Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of E. coli. Plasmid DNA is isolated from the transformed bacteria, restricted with the relevant restriction enzyme (thereby linearizing the unmutated plasmids), and then retransformed into E. coli. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control).

The verified mutant duplexes can be cloned into a replicable expression vector, if not already cloned into a vector of this type, and the resulting expression construct used to transform E. coli, such as strain E. coli BL21(DE3)pLysS, for high level production of the mutant protein, and subsequent purification thereof. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutant, it is generally desirable to first make a non-conservative substitution (e.g., Ala for Cys, His or Glu) and determine if activity is greatly impaired as a consequence. The properties of the mutagenized protein are then examined with particular attention to the kinetic parameters of $K_m$ and $k_{cat}$ as sensitive indicators of altered function, from which changes in binding and/or catalysis per se may be deduced by comparison to the native enzyme. If the residue is by this means demonstrated to be important by activity impairment, or knockout, then conservative substitutions can be made, such as Asp for Glu to alter side chain length, Ser for Cys, or Arg for His. For hydrophobic segments, it is largely size that will be altered, although aromatics can also be substituted for alkyl side chains. Changes in the normal product formation can indicate which step(s) of the reaction sequence have been altered by the mutation.

Other site directed mutagenesis techniques may also be employed with the nucleotide sequences of the invention. For example, restriction endonuclease digestion of DNA followed by ligation may be used to generate isopentenyl monophosphate kinase deletion variants, as described in section 15.3 of Sambrook et al. (*Molecular Cloning: A Laboratory Manual,* 2nd Ed., Cold Spring Harbor Laboratory Press, New York, N.Y. [1989]). A similar strategy may be used to construct insertion variants, as described in section 15.3 of Sambrook et al., supra.

Oligonucleotide-directed mutagenesis may also be employed for preparing substitution variants of this invention. It may also be used to conveniently prepare the deletion and insertion variants of this invention. This technique is well known in the art as described by Adelman et al. (*DNA* 2:183 [1983]). Generally, oligonucleotides of at least 25 nucleotides in length are used to insert, delete or substitute two or more nucleotides in the isopentenyl monophosphate kinase molecule. An optimal oligonucleotide will have 12 to 15 perfectly matched nucleotides on either side of the nucleotides coding for the mutation. To mutagenize the wild-type isopentenyl monophosphate kinase, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type isopentenyl monophosphate kinase inserted in the vector, and the second strand of DNA encodes the mutated form of isopentenyl monophosphate kinase inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type isopentenyl monophosphate kinase DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

The gene, or other nucleic acid molecule, encoding isopentenyl monophosphate kinase may be incorporated into any organism (intact plant, animal, microbe), or cell culture derived therefrom, that produces isopentenol monophosphate and ATP to effect the ATP-dependent conversion of these primary substrates to isopentenol diphosphate and its subsequent metabolic products, depending on the organism. By way of non-limiting example, an isopentenyl monophosphate kinase gene (or other nucleic acid molecule encoding isopentenyl monophosphate kinase) may be introduced into a plant in order to increase flux through the isoprenoid biosynthetic pathway that produces carotenoids, chlorophyll, plastoquinone, essential oils, resins, phytoalexins (such as casbene). The resulting transgenic plants can be selected for such improved characteristics as: improved plant fitness, improved defense capabilities against pests and pathogens, improved quality traits (such as color, flavor, vitamin content, antioxidants, nutrients and nutraceuticals) and improved yield of useful chemicals (such as pigments, vitamins, essential oils, resins, waxes and synthetic intermediates). Moreover, and by way of non-limiting example, a nucleic acid molecule encoding an isopentenyl monophosphate kinase protein can be subjected to mutagenesis in order to create isopentenyl monophosphate kinase mutant proteins that are resistant to isopentenyl monophosphate kinase-specific herbicides. Additionally, the isolated, recombinant isopentenyl monophosphate kinase proteins of the present invention can be used, for example, in studies to identify novel antibiotics, herbicides and anti-malarial drugs directed to isopentenyl monophosphate kinase.

Eukaryotic expression systems may be utilized for isopentenyl monophosphate kinase production since they are capable of carrying out any required posttranslational modifications and of directing the enzyme to the proper membrane location. A representative eukaryotic expression system for this purpose uses the recombinant baculovirus, *Autographa californica* nuclear polyhedrosis virus (AcNPV; M. D. Summers and G. E. Smith, *A Manual of Methods for Baculovirus Vectors and Insect Cell Culture Procedures* [1986]; Luckow et al., *Bio-technology* 6:47–55 [1987]) for expression of the isopentenyl monophosphate kinase of the invention. Infection of insect cells (such as cells of the species *Spodoptera frugiperda*) with the recombinant baculoviruses allows for the production of large amounts of the isopentenyl monophosphate kinase protein. In addition, the baculovirus system has other important advantages for the production of recombinant isopentenyl monophosphate kinase. For example, baculoviruses do not infect humans and can therefore be safely handled in large quantities. In the baculovirus system, a DNA construct is prepared including a DNA segment encoding isopentenyl monophosphate kinase and a vector. The vector may comprise the polyhedron gene promoter region of a baculovirus, the baculovirus flanking sequences necessary for proper cross-over during recombination (the flanking sequences comprise about 200–300 base pairs adjacent to the promoter sequence) and a bacterial origin of replication which permits the construct to replicate in bacteria. The vector is constructed so that (i) the DNA segment is placed adjacent (or operably linked or "downstream" or "under the control of") to the polyhedron gene promoter and (ii) the promoter/isopentenyl monophosphate kinase combination is flanked on both sides by 200–300 base pairs of baculovirus DNA (the flanking sequences).

To produce the isopentenyl monophosphate kinase DNA construct, a cDNA clone encoding the full length isopentenyl monophosphate kinase is obtained using methods such as those described herein. The DNA construct is contacted in a host cell with baculovirus DNA of an appropriate baculovirus (that is, of the same species of baculovirus as the promoter encoded in the construct) under conditions such that recombination is effected. The resulting recombinant baculoviruses encode the full isopentenyl monophosphate kinase. For example, an insect host cell can be cotransfected or transfected separately with the DNA construct and a functional baculovirus. Resulting recombinant baculoviruses can then be isolated and used to infect cells to effect production of the isopentenyl monophosphate kinase. Host insect cells include, for example, *Spodoptera frugiperda* cells, that are capable of producing a baculovirus-expressed isopentenyl monophosphate kinase. Insect host cells infected with a recombinant baculovirus of the present invention are then cultured under conditions allowing expression of the baculovirus-encoded isopentenyl monophosphate kinase. Isopentenyl monophosphate kinase thus produced is then extracted from the cells using methods known in the art.

Other eukaryotic microbes such as yeasts may also be used to practice this invention. The baker's yeast *Saccharomyces cerevisiae,* is a commonly used yeast, although several other types are available. The plasmid YRp7 (Stinchcomb et al., *Nature* 282:39 [1979]; Kingsman et al., *Gene* 7:141 [1979]; Tschemper et al., *Gene* 10:157 [1980]) is commonly used as an expression vector in Saccharomyces. This plasmid contains the trp1 gene that provides a selection marker for a mutant strain of yeast lacking the ability to grow in the absence of tryptophan, such as strains ATCC No. 44,076 and PEP4-1 (Jones, *Genetics* 85:12 [1977]). The presence of the trp1 lesion as a characteristic of the yeast host cell genome then provides an effective environment for detecting transformation by growth in the absence of tryptophan. Yeast host cells are generally transformed using the polyethylene glycol method, as described by Hinnen (*Proc. Natl. Acad. Sci. USA* 75:1929 [1978]. Additional yeast transformation protocols are set forth in Gietz et al., *N.A.R.* 20(17):1425, 1992; Reeves et al., *FEMS* 99:193–197, 1992.

Suitable promoting sequences in yeast vectors include the promoters for 3-phosphoglycerate kinase (Hitzeman et al.,*J. Biol. Chem.* 255:2073 [1980]) or other glycolytic enzymes (Hess et al., *J. Adv. Enzyme Reg.* 7:149 [1968]; Holland et al., *Biochemistry* 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triose-phosphate isomerase, phosphoglucose isomerase, and glucokinase. In the construction of suitable expression plasmids, the termination sequences associated with these genes are also ligated into the expression vector 3' of the sequence desired to be expressed to provide polyadenylation of the mRNA and termination. Other promoters that have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

Cell cultures derived from multicellular organisms, such as plants, may be used as hosts to practice this invention. Transgenic plants can be obtained, for example, by transferring plasmids that encode isopentenyl monophosphate kinase and a selectable marker gene, e.g., the kan gene encoding resistance to kanamycin, into *Agrobacterium tumifaciens* containing a helper Ti plasmid as described in Hoeckema et al., *Nature* 303:179–181 [1983] and culturing the Agrobacterium cells with leaf slices of the plant to be transformed as described by An et al., *Plant Physiology* 81:301–305 [1986]. Transformation of cultured plant host cells is normally accomplished through *Agrobacterium tumifaciens,* as described above. Cultures of mammalian host cells and other host cells that do not have rigid cell membrane barriers are usually transformed using the calcium phosphate method as originally described by Graham and Van der Eb (*Virology* 52:546 [1978]) and modified as described in sections 16.32–16.37 of Sambrook et al., supra. However, other methods for introducing DNA into cells such as Polybrene (Kawai and Nishizawa, *Mol. Cell. Biol.* 4:1172 [1984]), protoplast fusion (Schaffner, *Proc. Natl. Acad. Sci. USA* 77:2163 [1980]), electroporation (Neumann et al.,*EMBO J.* 1:841 [1982]), and direct microinjection into nuclei (Capecchi, *Cell* 22:479 [1980]) may also be used. Additionally, animal transformation strategies are reviewed in Monastersky G. M. and Robl, J. M., *Strategies in Transgenic Animal Science,* ASM Press, Washington, D.C., 1995. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition, a gene regulating isopentenyl monophosphate kinase production can be incorporated into the plant along with a necessary promoter which is inducible. In the practice of this embodiment of the invention, a promoter that only responds to a specific external or internal stimulus is fused to the target cDNA. Thus, the gene will not be transcribed except in response to the specific stimulus. As long as the gene is not being transcribed, its gene product is not produced.

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., *Plant Molecular Biology* 7:235–243 [1986]). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a isopentenyl monophosphate kinase gene that previously has had its native promoter removed. This engineered gene is the combination of a promoter that responds to an external chemical stimulus and a gene responsible for successful production of isopentenyl monophosphate kinase.

In addition to the methods described above, several methods are known in the art for transferring cloned DNA into a wide variety of plant species, including gymnosperms, angiosperms, monocots and dicots (see, e.g., Glick and Thompson, eds., *Methods in Plant Molecular Biology,* CRC Press, Boca Raton, Fla. [1993], incorporated by reference herein). Representative examples include electroporation-facilitated DNA uptake by protoplasts in which an electrical pulse transiently permeabilizes cell membranes, permitting the uptake of a variety of biological molecules, including recombinant DNA (Rhodes et al., *Science*, 240:204–207 [1988]); treatment of protoplasts with polyethylene glycol (Lyznik et al., *Plant Molecular Biology*, 13:151–161 [1989]); and bombardment of cells with DNA-laden microprojectiles which are propelled by explosive force or compressed gas to penetrate the cell wall (Klein et al., *Plant Physiol.* 91:440–444 [1989] and Boynton et al., *Science*, 240:1534–1538 [1988]). Transformation of Taxus species can be achieved, for example, by employing the methods set forth in Han et al., *Plant Science*, 95:187–196 [1994], incorporated by reference herein. A method that has been applied to Rye plants (*Secale cereale*) is to directly inject plasmid DNA, including a selectable marker gene, into developing floral tillers (de la Pena et al., *Nature* 325:274–276 [1987]). Further, plant viruses can be used as vectors to transfer genes to plant cells. Examples of plant viruses that can be used as vectors to transform plants include the Cauliflower Mosaic Virus (Brisson et al., *Nature* 310:511–514 [1984]). Additionally, plant transformation strategies and techniques are reviewed in Birch, R. G., *Ann Rev Plant Phys Plant Mol Biol*, 48:297 [1997]; Forester et al., *Exp. Agric.*, 33:15–33 [1997]. The aforementioned publications disclosing plant transformation techniques are incorporated herein by reference, and minor variations make these technologies applicable to a broad range of plant species.

Each of these techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. A commonly used selectable marker gene is neomycin phosphotransferase II (NPT II). This gene conveys resistance to kanamycin, a compound that can be added directly to the growth media on which the cells grow. Plant cells are normally susceptible to kanamycin and, as a result, die. The presence of the NPT II gene overcomes the effects of the kanamycin and each cell with this gene remains viable. Another selectable marker gene which can be employed in the practice of this invention is the gene which confers resistance to the herbicide glufosinate (Basta). A screenable gene commonly used is the β-glucuronidase gene (GUS). The presence of this gene is characterized using a histochemical reaction in which a sample of putatively transformed cells is treated with a GUS assay solution. After an appropriate incubation, the cells containing the GUS gene turn blue. Preferably, the plasmid will contain both selectable and screenable marker genes.

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

Mammalian host cells may also be used in the practice of the invention. Examples of suitable mammalian cell lines include monkey kidney CVI line transformed by SV40 (COS-7, ATCC CRL 1651); human embryonic kidney line 293S (Graham et al., *J. Gen. Virol.* 36:59 [1977]); baby hamster kidney cells (BHK, ATCC CCL 10); Chinese hamster ovary cells (Urlab and Chasin, *Proc. Natl. Acad. Sci USA* 77:4216 [1980]); mouse sertoli cells (TM4, Mather, *Biol. Reprod.* 23:243 [1980]); monkey kidney cells (CVI-76, ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor cells (MMT 060562, ATCC CCL 51); rat hepatoma cells (HTC, MI.54, Baumann et al., *J. Cell Biol.* 85:1 [1980]); and TRI cells (Mather et al., *Annals N.Y Acad. Sci.* 383:44 [1982]). Expression vectors for these cells ordinarily include (if necessary) DNA sequences for an origin of replication, a promoter located in front of the gene to be expressed, a ribosome binding site, an RNA splice site, a polyadenylation site, and a transcription terminator site.

Promoters used in mammalian expression vectors are often of viral origin. These viral promoters are commonly derived from polyoma virus, Adenovirus 2, and most frequently Simian Virus 40 (SV40). The SV40 virus contains two promoters that are termed the early and late promoters. These promoters are particularly useful because they are both easily obtained from the virus as one DNA fragment that also contains the viral origin of replication (Fiers et al., *Nature* 273:113 [1978]). Smaller or larger SV40 DNA fragments may also be used, provided they contain the approximately 250-bp sequence extending from the HindIII site toward the BglI site located in the viral origin of replication.

Alternatively, promoters that are naturally associated with the foreign gene (homologous promoters) may be used provided that they are compatible with the host cell line selected for transformation.

An origin of replication may be obtained from an exogenous source, such as SV40 or other virus (e.g., Polyoma, Adeno, VSV, BPV) and inserted into the cloning vector. Alternatively, the origin of replication may be provided by the host cell chromosomal replication mechanism. If the vector containing the foreign gene is integrated into the host cell chromosome, the latter is often sufficient.

The use of a secondary DNA coding sequence can enhance production levels of isopentenyl monophosphate kinase in transformed cell lines. The secondary coding sequence typically comprises the enzyme dihydrofolate reductase (DHFR). The wild-type form of DHFR is normally inhibited by the chemical methotrexate (MTX). The level of DHFR expression in a cell will vary depending on the amount of MTX added to the cultured host cells. An additional feature of DHFR that makes it particularly useful as a secondary sequence is that it can be used as a selection marker to identify transformed cells. Two forms of DHFR are available for use as secondary sequences, wild-type DHFR and MTX-resistant DHFR. The type of DHFR used in a particular host cell depends on whether the host cell is DHFR deficient (such that it either produces very low levels of DHFR endogenously, or it does not produce functional DHFR at all). DHFR-deficient cell lines such as the CHO cell line described by Urlaub and Chasin, supra, are transformed with wild-type DHFR coding sequences. After transformation, these DHFR-deficient cell lines express functional DHFR and are capable of growing in a culture medium lacking the nutrients hypoxanthine, glycine and thymidine. Nontransformed cells will not survive in this medium.

The MTX-resistant form of DHFR can be used as a means of selecting for transformed host cells in those host cells that endogenously produce normal amounts of functional DHFR that is MTX sensitive. The CHO-K1 cell line (ATCC No. CL 61) possesses these characteristics, and is thus a useful cell line for this purpose. The addition of MTX to the cell culture medium will permit only those cells transformed with the DNA encoding the MTX-resistant DHFR to grow. The nontransformed cells will be unable to survive in this medium.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coli* K12 strain 294 (ATCC No. 31,446), *E. coli* strain W3110 (ATCC No. 27,325) *E. coli* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various Pseudomonas species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., *Genetic Engineering, Principles and Methods*, 12:275–296, Plenum Publishing Corp. [1990]; Hanahan et al., *Meth. Enxymol.*, 204:63 [1991].

As will be apparent to those skilled in the art, any plasmid vectors containing replicon and control sequences that are derived from species compatible with the host cell may also be used in the practice of the invention. The vector usually has a replication site, marker genes that provide phenotypic selection in transformed cells one or more promoters, and a polylinker region containing several restriction sites for insertion of foreign DNA. Plasmids typically used for transformation of *E. coli* include pBR322, pUC18, pUC19, pUCl18, pUC119, and Bluescript M13, all of which are described in sections 1.12–1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. *Nature* 375:615 [1978]; Itakura et al., *Science* 198:1056 [1977]; Goeddel et al., *Nature* 281:544 [1979]) and a tryptophan (trp) promoter system (Goeddel et al., *Nucl. Acids Res.* 8:4057 [1980]; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., *Cell* 20:269 [1980]).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, *Biochemistry* W. H. Freeman and Company, New York, N.Y., p. 769 [1988]), and can be used as signal sequences in appropriate eukaryotic host cells. Yeast signal sequences, as for example acid phosphatase (Arima et al., *Nuc. Acids Res.* 11:1657 [1983]), alpha-factor, alkaline phosphatase and invertase may be used to direct secretion from yeast host cells. Prokaryotic signal sequences from genes encoding, for example, LamB or OmpF (Wong et al., *Gene* 68:193 [1988]), MalE, PhoA, or beta-lactamase, as well as other genes, may be used to target proteins from prokaryotic cells into the culture medium.

The isopentenyl monophosphate kinase protein having the sequence set forth in SEQ ID NO:2 includes a putative amino terminal membrane insertion sequence at residues 1 through 98, and in the embodiment shown in SEQ ID NO:2 directs the enzyme to plastids. Alternative trafficking sequences from plants, animals and microbes can be employed in the practice of the invention to direct the gene product to the cytoplasm, endoplasmic reticulum, mitochondria or other cellular components, or to target the protein for export to the medium. These considerations apply to the overexpression of isopentenyl monophosphate kinase, and to direction of expression within cells or intact organisms to permit gene product function in any desired location.

The construction of suitable vectors containing DNA encoding replication sequences, regulatory sequences, phenotypic selection genes and the isopentenyl monophosphate kinase DNA of interest are prepared using standard recombinant DNA procedures. Isolated plasmids and DNA fragments are cleaved, tailored, and ligated together in a specific order to generate the desired vectors, as is well known in the art (see, for example, Sambrook et al., supra).

As discussed above, isopentenyl monophosphate kinase variants are preferably produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan.

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60–1.61 and sections 3.38–3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (*Nucleic Acids Res.* 9:6103–6114 [1982]), and Goeddel et al. (*Nucleic Acids Res.*, supra).

The following examples merely illustrate the best mode now contemplated for practicing the invention, but should not be construed to limit the invention.

EXAMPLE 1

Substrates, Cloning Strategies and Enzymatic Assays

Unless stated otherwise, the following substrates, cloning strategies and enzymatic assays were utilized in the cloning, expression and characterization of mint isopentenyl monophosphate kinase (SEQ ID NO:2), and its bacterial ortholog (SEQ ID NO:6).

Substrates: [1-$^3$H]Dimethylallyl diphosphate (555 GBq/mmol$^{-1}$) was purchased from American Radiolabeled Chemicals and was adjusted to a specific activity of 2.13 GBq/mmol$^{-1}$ by dilution with the unlabeled compound (purchased from Sigma). [4-$^{14}$C]Isopentenyl diphosphate (2.13 GBq/mmol$^{-1}$) was obtained from DuPont/NEN. [1-$^3$H]Dimethylallyl monophosphate and [4-$^{14}$C] isopentenyl monophosphate were generated enzymatically by treatment of the parent diphosphates (0.17 μmol of each) with apyrase (Sigma, catalogue number A6410) under the following conditions: 10 units of apyrase in 200 μl of 0.2 M succinate buffer, pH 6.0, for 5 min at 23° C. Extended incubation (1 h) under the same conditions with a mixture of apyrase and acid phosphatase (Sigma, catalogue number A6535) yielded [1-$^3$H]dimethylallyl alcohol and [4-$^{14}$C] isopentenol. Each phosphorylated product was purified by semi-preparative ion-pair HPLC, and identity was established by dephosphorylation and subsequent GC-MS analysis of the derived alcohol using methods modified from a published protocol (Lange, B. M. & Croteau R., *Arch. Biochem. Biophys.*, 365:170–174 [1999]). [1-$^{14}$C]1-Deoxy-D-xylulose-5-phosphate and [2-$^{14}$C]2-C-methyl-D-erythritol were prepared enzymatically from [2-$^{14}$C]pyruvic acid (DuPont/NEN, 0.59 GBq/mmol$^{-1}$) as described previously (Lange, B. M., Wildung, M., McCaskill, D. & Croteau R., *Proc. Natl. Acad. Sci. USA,* 95:2100–2104 [1998]; Lange, B. M. & Croteau R., *Arch. Biochem. Biophys.,* 365:170–174 [1999]). R,S-[2-$^{14}$C]Mevalonic acid (2.12 GBq/mmol$^{-1}$) was purchased from DuPont/NEN.

Bacterial Strains and Plasmid Constructs: A λZAP cDNA library was constructed from mRNA obtained (Logemann, J., Schell, J. & Willmitzer, L., *Anal. Biochem.,* 163:16–20 [1987]) from isolated peppermint oil gland secretory cells (McCaskill, D. & Croteau, R., *Planta,* 197:49–56 [1995]) according to the manufacturer's instructions (Stratagene). Randomly picked and purified clones were excised in vivo and inserts of the resulting pBluescript SK[31] phagemids were partially sequenced from both ends. An apparently full-length, peppermint IP kinase clone (designated ml100) (SEQ ID NO:1) was acquired by this means and was used as a template to amplify by PCR the portion of the sequence of SEQ ID NO:1 extending from residue 3 to residue 1217, using the primers 5'-ATGGCTTCCTCCT-CCCATTTCCTC-3' (forward) (SEQ ID NO:3) and 5'-TTCAGCATCCTGAGGAAAAGACGG-3' (reverse) (SEQ ID NO:4), which was subsequently cloned into the expression vector pBAD TOPO TA (Invitrogen). *E. coli* strain BL21-CodonPlus-RIL (F[31] ompT, hsdS($r_B^-m_B^-$), dcm[30], Tet$^R$, gal, endA, Hte, [argU, ileY, leuW, Cam$^R$]; Invitrogen) served as host in the transformation. The putative *E. coli* IP kinase gene (SEQ ID NO:5) was amplified by PCR using the primers 5'-ATGCGGACACAGTGGCCCTC-3' (forward) (SEQ ID NO:7) and 5'-AAGCATGGCTCTGTGCAATG-3' (reverse) (SEQ ID NO:8), and genomic DNA from the strain K-12 MG1655 (wild-type) as a template. For expression, the amplicon was cloned into pBAD TOPO TA (Invitrogen) and transformed into *E. coli* strain TOP10 One Shot (F$^-$, mcrA, Δ(mrr-hsdRMS-mcrBC) φ80lacZΔM15, ΔlacX74, recA1, deoR, araD139 Δ(ara-leu)7697, galU, galK, rpsL, (Str$^R$), endA1, nupG; Invitrogen).

Kinase Assays and Product Identification: Bacterial cells were grown in LB medium supplemented with appropriate antibiotics (ampicillin and chloramphenicol for the expression of the putative peppermint kinase (SEQ ID NO:1), ampicillin for the expression of the putative *E. coli* kinase (SEQ ID NO:5)) to an OD$_{600}$ of 0.2, then treated with either 0.02% arabinose (induction of transgene expression) or 0.02% glucose (repression of transgene expression), and incubated at 20° C. for 20 h. After harvest by centrifugation (1800×g, 5 min), the cells were resuspended in 2 ml of assay buffer (100 mM Tris/HCl (pH 7.5) containing 20 mM MgCl$_2$, 20 mM ATP, and 1 mM DTT), and disrupted by sonication at 0–4° C.; the protein content of the resulting homogenate was determined using the Bio-Rad protein assay. To aliquots containing 400 μg of total protein, 0.79 nmol of the appropriate substrate was added, and the mixture was incubated at 30° C. for 5–60 min. Cell debris was pelleted by centrifugation (13,000 rpm, bench-top centrifuge), protein was removed by filtration through a Nanosep cartridge (10 kDa cut-off; Pall Filtron), and the filtrate was analyzed by reversed-phase ion-pair radio-HPLC using a modification of a previously published method (McCaskill, D. & Croteau, R., *Anal. Biochem.,* 215:142–149 [1993]; column: Adsorbosphere HS C18 (Alltech, 5 μm particle size, 4.6 mm i.d., 250 mm length); solvents: (A) 10 mM tetrabutylammonium acetate (pH 6), (B) 10 mM tetrabutylammonium acetate in 70% aq. methanol (pH 6), (C) 70% aq. methanol; gradient: 100% (A) (hold for 10 min), gradient to 80% (B)/20% (A) (65 min), hold for 10 min, gradient to 100% (C) (10 min), hold for 10 min; flow rate: 1 ml/min$^{-1}$; retention times: IPP, 72.6 min; DMAPP, 70.4 min; IP, 64.6 min; DMAP, 63.7 min; isopentenol, 32.9 min; dimethylallyl alcohol, 34.6 min; DXP, 49.4 min; DX, 21.2 min; MEP, 46.8 min; MVA, 32.6 min.

Partial Purification of Recombinant *E. coli* IP Kinase: Bacteria were grown as described herein. After centrifugation (1800×g, 5 min), cells were resuspended in 1.5 ml of lysis buffer (20 mM sodium phosphate (pH 7.8) containing 500 mM NaCl), incubated with 100 μg egg white lysozyme (15 min on ice), and sonicated using three 10-second bursts at medium intensity. The crude lysate was treated with RNase (5 μg, 10 min, 30° C.) and DNase (5 μg, 10 min, 30°

C.), insoluble debris was removed by centrifugation (15,000×g, 10 min), and the supernatant was transferred to a tube containing 4 ml of ProBond resin (Invitrogen) pre-equilibrated with lysis buffer. To bind the recombinant enzyme, which was expressed as a fusion protein containing a 6×His affinity tag, the suspension was gently agitated for 20 min at 4° C. After brief centrifugation (700×g, 2 min), the supernatant was carefully decanted and the remaining resin was washed twice with 40 ml of lysis buffer. The resin was transferred to a gravity flow column and washed with an additional 5 ml of lysis buffer, and the recombinant protein was then eluted with 3 ml of elution buffer (20 mM potassium phosphate (pH 6.4) containing 500 mM NaCl and 300 mM imidazole). The eluent was transferred to Econo-Pac 10-DG columns (Bio-Rad) and the IP kinase was desalted by elution with 100 mM Tris/HCl buffer (pH 7.5). Aliquots of this partially purified preparation (15 µg total protein) were assayed for kinase activity as described herein.

Isolation of and Feeding Studies with Peppermint Oil Gland Secretory Cells: Leaves (15–20 g; <10 mm in length) were excised from peppermint plants (*Mentha x piperita* L. cv. Black Mitcham) and the oil gland secretory cells were isolated by the glass bead abrasion method (McCaskill, D. & Croteau, R., *Planta*, 197:49–56 [1995]). Following isolation, the secretory cells were washed with 25 mM Tris/HCl buffer (pH 7.3) containing 200 mM sorbitol, 10 mM sucrose, 5 mM $MgCl_2$, 10 mM KCl, 1 mM ethyleneglycol bis(β-aminoethyl ether), 8.5 mM $Na_2HPO_4$, and 0.1 mM $Na_4P_2O_7$, and then suspended in the same buffer supplemented with 2 mM ATP, 0.1 mM NADPH, 0.1 mM $NAD^+$, 5 mM phosphoenol pyruvate, and 5 mM glucose-6-phosphate. Cell density was determined using a hemocytometer and was adjusted to 1–2×10⁵ cellular disks (each containing eight secretory cells) per milliliter suspension. Aliquots (1–1.5 ml) were transferred to 15 ml screw-cap glass vials, and the suspended cells were aerated and incubated at 23° C. for 2 h. At the end of the incubation period, the suspension was extracted three times with 1 ml diethyl ether. The combined organic extract was washed with 1 ml of 1 M $Na_2CO_3$ and dried over $Na_2SO_4$. An aliquot was removed for liquid scintillation counting and, to the remainder, authentic standards (10–50 µg each) of isopentenol, dimethylallyl alcohol, geraniol, farnesol, limonene, menthone, menthol, pulegone, humulene, and caryophyllene were added. These extracts were then slowly concentrated on ice under a gentle stream of $N_2$ to ~200 µl, and were then transferred to conical glass vials and further concentrated to 5–10 µl at 20° C. in preparation for chromatographic analysis.

Radio-GLC Analysis of Peppermint Isoprenoids: Radio-GC was performed according to a published method (Croteau, R. & Satterwhite, D. M. *J. Chromatog.* 500:349–354 [1990]) with several modifications; 0.25 mm i.d.×30 m AT 1000 fused silica column with 0.2 µm film thickness (Alltech); helium carrier gas at 3–6 ml/min$^{-1}$; temperature program from 70 to 200° C. at 5° C./min$^{-1}$; injector at 200° C.; thermal conductivity detector at 220° C. and 140 mA; propane quench gas at 10–15 ml/min$^{-1}$. The relative peak area corresponding to each biosynthetic product was converted to dpm as a fraction of the total radioactivity determined by liquid scintillation counting prior to concentration. The absolute amount of each component formed was then calculated based on the specific activity of the corresponding radiolabeled substrate.

EXAMPLE 2

Cloning of a Nucleic Acid Molecule Encoding Isopentenyl Monophosphate Kinase from Peppermint The oil glands (glandular trichomes) of mint species are highly specialized for the production of monoterpenes and sesquiterpenes, and the secretory cells of these structures are thus highly enriched in the machinery for terpenoid biosynthesis (Lange, B. M. & Croteau, R., *Curr. Opin. Plant Biol.,* 2:139–144 [1999]). As described in Example 1, 1300 random clones obtained from an enriched cDNA library, constructed specifically from mRNA isolated from peppermint glandular trichome secretory cells as described in Example 1 herein, were analyzed. Since the most advanced, defined intermediate of the plastidial DXP pathway to isoprenoids is 2-C-methyl-D-erythritol-4-phosphate (Duvold, T., Bravo, J. M., Pale-Grosdemange, C. & Rohmer, M., *Tetrahedron Lett.,* 38:4769–4772 [1997]; Duvold, T., Calí, P., Bravo, J. M. & Rohmer M., *Tetrahedron Lett.,* 38:6181–6184 [1997]; Sagner, S., Eisenreich, W., Fellermeier, M., Latzel, C., Bacher, A. & Zenk, M. H., *Tetrahedron Lett.* 39:2091–2094 [1998]), and the end product of the pathway is IPP (McCaskill, D. & Croteau R., *Tetrahedron Lett.,* 40:653–656 [1999]; Arigoni, D., Eisenreich, W., Latzel, C., Sagner, S., Radykewicz, T., Zenk, M. H. & Bacher, A, *Proc. Natl. Acad. Sci. USA,* 96:1309–1314 [1999]), a phosphorylation step must occur at some point during this reaction sequence. Accordingly, metabolite phosphokinases were sought, but only two clones with similarity to adenylate kinases were noted by searching the common databases. However, a more detailed search of the Prosite database (http://www.expasy.ch/prosite) revealed another more promising clone (designated ml100) (SEQ ID NO:1) which shared a region of high sequence similarity to the putative ATP-binding domain of the GHMP family of kinases (Tsay, Y. H. & Robinson, G. W., *Mol. Cell. Biol.,* 11:620–631 [1991]). The deduced amino acid sequence of this peppermint clone (SEQ ID NO:2) additionally showed significant homology to a chromoplast-directed protein of unknown function from ripening tomato fruits (Lawrence, S. D. Cline, K. & Moore, G. A., *Plant Mol. Biol.,* 33:483–492 [1997]) and to a number of hypothetical proteins from several eubacteria.

To examine the possible function of the peppermint clone ml100 (SEQ ID NO:1), the coding region (nucleotides 3 to 1217 of SEQ ID NO:1) was amplified by PCR, transferred into the expression vector pBAD TOPO TA (to yield pBAD-MPK), and, for convenient purification, expressed as a 6×His fusion protein in *E. coli* BL21-CodonPlus-RIL cells (which contain an extra plasmid encoding rare tRNAs that specify Arg, Leu and Ile). However, the expressed enzyme strongly tended to form inclusion bodies, and, even after several attempts to increase the soluble activity by decreasing the amount of arabinose added for induction (0.001–0.01%) and by prolonging the incubation at lower temperatures (8–15° C.), soluble protein could not be obtained in sufficient quantity for affinity-based ($Ni^{2+}$-binding) purification. Thus, crude extracts of sonicated, transformed cells served as the enzyme source for kinase assays. As a control, *E. coli* harboring pBAD-MPK were treated with 0.02% glucose which leads to repression of transgene expression. Consistently, the expressed recombinant peppermint kinase gave detectably elevated levels of activity with isopentenol monophosphate (IP; 1.43 pmol (s g protein)$^{-1}$ and isopentenol (ISO; 0.10 pmol/s·g protein as substrates, when compared to the *E. coli* background (repressed) controls (IP, 0–1.0 pmol/s·g protein; ISO, 0.08 pmol/s·g protein (Table 1).

TABLE 1

Substrate specificity of recombinant IP kinases

| Substrate | Peppermint* | E. coli* (repressed) | E. coli* (induced) | E. coli (partially purified) |
|---|---|---|---|---|
| | | Rate [pmol/s · g protein]† | | |
| IP | 1.43 | <1.0‡ | 2.41 | 178 ± 81 |
| ISO | 0.10 | 0.08 | 0.10 | 79 ± 24 |
| DMAP | n.d. | n.d. | n.d. | n.d. |
| DMA | <0.01 | <0.01 | <0.01 | 11 ± 5 |
| DXP | <0.1§ | <0.1§ | <0.1§ | n.d. |
| DX | <0.1§ | <0.1§ | <0.1§ | n.d. |
| MEP | <0.2§ | <0.2§ | <0.2§ | n.d. |
| MVA | n.d. | n.d. | n.d. | n.d. |

*These crude extracts contained high phosphatase activity; the rates given are thus minimums.
†Rates are given as averages of two to five separate experiments, with standard deviation where appropriate.
‡The kinase activity in this assay varied but was always below the rate shown in Table 1.
§In most of these assays, no kinase activity was observed; in some cases, minor levels of the apparent product were detected.
n.d. not detectable.

No phosphokinase activity was detected with dimethylallyl monophosphate (DMAP) or MVA as substrate. Kinase activity with dimethylallyl alcohol (DMA) as a substrate, under the standard assay conditions, was always detectable, but never exceeded 0.01 pmol/s·g protein. With DXP, deoxylylulose (DX) and MEP as substrates, kinase activity of less than 0.2 pmol/s·g protein was occasionally detected but in most experiments no activity was observed. Because these assays with crude extracts were severely compromised by the presence of competing phosphatases (as evidenced by the production of the corresponding dephosphorylated products upon HPLC analysis), the conversion rates observed must be regarded as minimum values.

EXAMPLE 3

Cloning of a Nucleic Acid Molecule Encoding Isopentenyl Monophosphate Kinase from *Escherichia coli*

As an alternative to further expression studies with the recombinant peppermint enzyme (SEQ ID NO:2), such as by truncation of the putative plastidial targeting sequence as an attempt to minimize protein misfolding (Williams, D. C. et al., (1998) *Biochemistry* 37:12213–12220.), the *E. coli* orthologue (SEQ ID NO:6) of the peppermint kinase (SEQ ID NO:2) was evaluated. This *E. coli* gene (ychB) (SEQ ID NO:1), which was found by database homology searching and which is located at 27.2 min of the chromosomal map, was amplified by PCR and transferred into pBAD TOPO TA (to yield pBAD-ECK), for similar expression as a 6×His fusion protein. Assay of crude extracts gave results similar to those obtained with the recombinant peppermint enzyme (Table 1). However, in this instance, the expressed, soluble enzyme, produced upon induction with 0.02% arabinose, allowed a useful one-step affinity-based purification with the $Ni^{2+}$-binding column. This partially purified protein readily catalyzed the conversion of IP to IPP (178±81 pmol/s·g protein), ISO to IP (79±24 pmol/s·g protein), and DMA to DMAP (11±5 pmol/s·g protein); however, no phosphorylating activity was detectable with DMAP, DXP, DX, MEP or MVA as substrate (Table 1). This kinase activity (with IP as a substrate) was dependent upon the presence of $MgCl_2$ as divalent cation and ATP as phosphate donor, whereas CTP, UTP and GTP did not serve as alternate phosphate donors. As a control, pBAD-ECK expression in *E. coli* was repressed by addition of 0.02% glucose, and the extracted proteins were subjected to the same purification step as the peppermint IPK (SEQ ID NO:2) described in Example 2, herein; kinase assays with these enzyme preparations yielded no detectable activity with any of the above substrates. These results with the enzyme products of the peppermint ml100 clone (SEQ ID NO:1) and the *E. coli* ychB clone (SEQ ID NO:5) suggest that the peppermint gene (SEQ ID NO:1) encodes an isopentenyl monophosphate kinase (IPK) that is involved in the DXP pathway to isoprenoids.

EXAMPLE 4

Sequence Analysis

The peppermint IPK gene (SEQ ID NO:1) contains an open reading frame of 1218 nucleotides. The first 98 deduced amino acid residues display the general characteristics of plastidial targeting sequences (von Heijne, G., Steppuhn, J. & Herrmann, R. G., *Eur. J Biochem.*, 180:535–545 [1989]), and, when this putative leader peptide is excluded, a mature protein of 308 amino acids with a predicted size of about 33 kDa is obtained. The gene encoding *E. coli* IPK (SEQ ID NO:5) consists of 852 nucleotides, which corresponds to an enzyme of 283 amino acids with a size of 31 kDa (SEQ ID NO:6). Database sequence comparison of translated, putative IPK genes from several different organisms revealed very high similarity/identity scores within the plant kingdom (>81.6/74.8% for presumptive orthologues found in tomato (SEQ ID NO:9 encoding the protein of SEQ ID NO:10) and *Arabidopsis thaliana* (SEQ ID NO:11 encoding the protein of SEQ ID NO:12)), and a high degree of sequence variation among eubacteria (39.0–70.2/25.6–62.5%) and between plants and eubacteria (38.3–48.8/28.5–38.6%). The isopentenyl diphosphate kinases appear to share a conserved, glycine-rich sequence motif ($PXGAGLGGGSSNAAX_{(15-16)}(K/R)$) (SEQ ID NO:13) similar to the conserved sequence $PXXXGL(G/S)SS(A/G)XX_{(12-25)}$ (K/R) (SEQ ID NO:14) found in the GHMP family of kinases, including galactokinase, homoserine kinase, mevalonate kinase and phosphomevalonate kinase (Tsay, Y. H. & Robinson, G. W., *Mol. Cell. Biol.*, 11:620–631 [1991]). A related motif is also present in protein kinases (Hanks, S. K., Quinn, A. M. & Hunter, T., *Science*, 241:42–52 [1988]). The gene for the *A. thaliana* IPK orthologue is located on chromosome 2 (AC005168; BAC F12C20; PID g3426035), near the marker B68, and contains 10 introns. Neither the intron/exon organization nor a phylogenetic analysis reveals a direct evolutionary relationship between different classes of the GHMP kinase family (data not shown). A detailed survey of the available microbial genome project databases did not indicate the IPK gene (SEQ ID NO:1) to be part of a cluster with other (potential) genes of the DXP pathway.

EXAMPLE 5

Incorporation of IP into Isoprenoids of Peppermint Secretory Cells

Although IP was shown to be the preferred substrate of both peppermint IPK (SEQ ID NO:2) and *E. coli* IPK (SEQ ID NO:6), it remained to be directly demonstrated that IP was an intermediate of the DXP pathway. Previous experiments with isolated peppermint oil gland secretory cells had demonstrated that the MVA pathway in these cells is blocked at an early stage, and that IPP utilized for both monoterpene and sesquiterpene biosynthesis is synthesized exclusively in the plastids from pyruvate (McCaskill, D. & Croteau, R., *Planta,* 197:49–56 [1995]), almost certainly via the DXP pathway (Eisenreich, W. et al., *Tetrahedron Lett.,* 38:3889–3892 [1997]). The high degree of metabolic specialization and the ability to synthesize monoterpenes and sesquiterpenes de novo from basic precursors, including phosphorylated intermediates (McCaskill, D. & Croteau, R., *Planta,* 197:49–56 [1995]), made the isolated secretory cells an ideal model system to establish that IP was an intermediate of the DXP pathway, and the activity of IP kinase, in vivo.

Thus, isolated secretory cells were incubated under comparable conditions with several radiolabeled substrates (ISO, IP, IPP, DMA, DMAP, DMAPP), and, after extraction of products with diethyl ether, the incorporation into monoterpenes and sesquiterpenes was quantified by liquid scintillation counting and radio-GC analysis of these volatile metabolites (Table 2).

TABLE 2

Conversion of potential $C_5$-precursors into terpenoids by isolated peppermint oil gland secretory cells

| Precursor | Total Terpenoids* ($C_{10} + C_{15}$) |
|---|---|
| IPP | 561 |
| IP | 43 |
| ISO | 304 |
| DMAPP | 4 |
| DMAP | 6 |
| DMA | n.d. |

*Rates of incorporation into total monoterpenoids and sesquiterpenoids are given in pmol (h $10^5$ cell clusters)$^{-1}$ (average of two experiments), and include geraniol and farnesol released by phosphatases from the intermediates geranyl diphosphate ($C_{10}$) and farnesyl diphosphate ($C_{15}$).
n.d. not detectable.

Since the IP kinase (SEQ ID NO:2) is plastidial, as is monoterpene biosynthesis, whereas sesquiterpene biosynthesis is cytosolic (McCaskill, D. & Croteau, R., *Planta,* 197:49–56 [1995]), uptake and partitioning differences between the $C_5$ precursors influence the distribution between monoterpene and sesquiterpene biosynthetic pathways. In a similar fashion, endogenous phosphatases of both plastidial and cytosolic origin can complicate the partitioning of precursors into the pathways of these compartments. Thus, as a measure of the conversion efficiency of each $C_5$ precursor, total monoterpenoids ($C_{10}$) and sesquiterpenoids ($C_{15}$), including geraniol and farnesol released by phosphatases from the corresponding diphosphate ester intermediates, were recorded. By this measure, IPP was most readily converted to terpenoid end-products as expected (561 pmol (h $10^5$ cell clusters)$^{-1}$), followed by ISO (304 pmol (h $10^5$ cell clusters)$^{-1}$), most likely reflecting efficient plastidial uptake of this low molecular weight alcohol, and then IP (43 pmol (h $10^5$ cell clusters)$^{-1}$). DMAPP and DMAP were not very efficient precursors of terpenoids in secretory cells (<6 pmol (h $10^5$ cell clusters)$^{-1}$), and the incorporation of DMA was negligible. Although ISO, likely because of uptake rates, and the more advanced precursor IPP were transformed to terpenoids in vivo at higher rates than was IP, the latter was incorporated at a rate (43 pmol (h $10^5$ cell clusters)$^{-1}$) comparable to that observed previously with pyruvate (67 pmol (h $10^5$ cell clusters)$^{-1}$) (McCaskill, D. & Croteau, R., *Planta,* 197:49–56 [1995]), an efficient, established precursor of the DXP pathway.

Although IP and ISO were shown to be efficient in vitro substrates for this newly defined kinase (SEQ ID NO:2), and the role of this kinase (SEQ ID NO:2) was demonstrated by in vivo feeding studies, several steps of the mevalonate-independent pathway still remain to be elucidated, and it cannot be ruled out that the required phosphorylation step also may occur with intermediates other than IP.

EXAMPLE 6

Characteristics of Presently Preferred Nucleic Acid Molecules Encoding Isopentenyl Monophosphate Kinase Proteins of the Invention Presently preferred nucleic acid molecules encoding isopentenyl monophosphate kinase proteins of the present invention are capable of hybridizing to the antisense, complementary nucleic acid sequence of the nucleic acid molecule having the sequence set forth in SEQ ID NO:1 under stringent conditions. Presently preferred, high stringency conditions are: hybridization in 5×SSC at 65° C. for 16 hours, followed by two washes in 2×SSC at room temperature (20° C. to 25° C.) for 15 minutes per wash, followed by two washes in 0.5×SSC at 65° C. for 20 minutes per wash. Presently preferred, moderate stringency conditions are: hybridization in 5×SSC at 65° C. for 16 hours, followed by two washes in 2×SSC at room temperature (20° C. to 25° C.) for 20 minutes per wash, followed by one wash in 1.0×SSC at 55° C. for 30 minutes. Presently preferred, low stringency conditions are: hybridization in 6×SSC at room temperature (20° C. to 25° C.) for 16 hours, followed by two washes in 3.0×SSC at room temperature (20° C. to 25° C.) for 20 minutes per wash.

The ability of the nucleic acid molecules of the present invention to hybridize to the complementary sequence of the nucleic acid sequence set forth in SEQ ID NO:1, can be determined utilizing the technique of hybridizing radiolabelled nucleic acid probes to nucleic acids immobilized on nitrocellulose filters or nylon membranes as set forth, for example, at pages 9.52 to 9.55 of *Molecular Cloning, A Laboratory Manual* (2nd edition), J. Sambrook, E. F. Fritsch and T. Maniatis eds., the cited pages of which are incorporated herein by reference.

EXAMPLE 7

Characteristics of Presently Preferred Isolated Recombinant Isopentenyl Monophosphate Kinase Proteins of the Invention Presently preferred, isolated, recombinant isopentenyl monophosphate kinase proteins of the present invention have a mature molecular weight (i. e., excluding any amino terminal targeting sequence) of from about 30 kDa to about 36 kDa; utilize $Mg^{2+}$ (or other divalent metal ion) and ATP as cofactors; utilize isopentenol, isopentenyl monophosphate or dimethylallyl alcohol as substrates; have a pH optimum in the range of from about 6.0 to about 8.0, and have a Km (utilizing isopentenyl monophosphate as substrate and ATP as cofactor) of less than 1 mM.

EXAMPLE 8

Representative Examples of Nucleic Acid Molecules Useful in the Methods of the Present Invention In one aspect, the present invention provides methods of altering the level of expression of isopentenyl monophosphate kinase in a host cell comprising introducing into the host cell a nucleic acid molecule encoding an isopentenyl monophosphate kinase under conditions that enable expression of the isopentenyl monophosphate kinase in the host cell. Representative examples of nucleic acid molecules, encoding an isopentenyl monophosphate kinase protein, that are useful in the methods of the present invention to alter the level of expression of isopentenyl monophosphate kinase in a host cell include the nucleic acid molecules having the sequences set forth in SEQ ID NO:1 (encoding the peppermint isopentenyl monophosphate kinase of SEQ ID NO:2), SEQ ID NO:5 (encoding the *E. coli* isopentenyl monophosphate kinase of SEQ ID NO:6), SEQ ID NO:9 (encoding the *Lycopersicon esculentum* isopentenyl monophosphate kinase of SEQ ID NO:10), SEQ ID NO:11 (encoding the Arabidopsos isopentenyl monophosphate kinase of SEQ ID NO:12) and SEQ ID NO:15 (encoding the Synechocystis sp. isopentenyl monophosphate kinase of SEQ ID NO:16).

In another aspect, the present invention provides methods for reducing the level of expression of isopentenyl monophosphate kinase in a host cell comprising introducing into the host cell a nucleic acid molecule, encoding at least a portion of an isopentenyl monophosphate kinase, oriented in antisense orientation with respect to a promoter sequence under conditions enabling transcription of the antisense nucleic acid molecule. Representative examples of nucleic acid molecules, encoding an isopentenyl monophosphate kinase protein, that are useful in the practice of the present invention to reduce the level of expression of isopentenyl monophosphate kinase in a host cell include the nucleic acid molecules having the sequences set forth in SEQ ID NO:1 (encoding the peppermint isopentenyl monophosphate kinase of SEQ ID NO:2), SEQ ID NO:5 (encoding the *E. coli* isopentenyl monophosphate kinase of SEQ ID NO:6), SEQ ID NO:9 (encoding the *Lycopersicon esculentum* isopentenyl monophosphate kinase of SEQ ID NO:10), SEQ ID NO:11 (encoding the Arabidopsos isopentenyl monophosphate kinase of SEQ ID NO:12) and SEQ ID NO:15 (encoding the Synechocystis sp. isopentenyl monophosphate kinase of SEQ ID NO:16).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule encoding an isopentenyl monophosphate kinase, said isolated nucleic acid molecule hybridizing to the nucleic acid molecule consisting of the sequence set forth in SEQ ID NO: 1, or the complement of the sequence set forth in SEQ ID NO: 1, under moderately stringent conditions, provided that said isolated nucleic acid molecule does not consist of a nucleic acid sequence selected from the group consisting of SEQ ID NO:5, SEQ ID NO:9, SEQ ID NO:11 and SEQ ID NO:15.

2. An isolated nucleic acid molecule of claim 1 encoding a prokaryotic isopentenyl monophosphate kinase.

3. An isolated nucleic acid molecule of claim 1 encoding a eukaryotic isopentenyl monophosphate kinase.

4. An isolated nucleic acid molecule of claim 3 encoding a eukaryotic plant isopentenyl monophosphate kinase.

5. An isolated nucleic acid molecule of claim 4 encoding a gymnosperm isopentenyl monophosphate kinase.

6. An isolated nucleic acid molecule of claim 4 encoding an angiosperm isopentenyl monophosphate kinase.

7. An isolated nucleic acid molecule of claim 6 encoding an essential oil plant isopentenyl monophosphate kinase.

8. An isolated nucleic acid molecule of claim 7 encoding an isopentenyl monophosphate kinase from a member of the family Lamiaceae.

9. An isolated nucleic acid molecule of claim 8 encoding a Mentha isopentenyl monophosphate kinase.

10. An isolated nucleic acid molecule of claim 9 encoding a *Mentha piperita* isopentenyl monophosphate kinase.

11. An isolated nucleic acid molecule of claim 10 encoding an isopentenyl monophosphate kinase protein consisting of the amino acid sequence set forth in SEQ ID NO:2.

12. An isolated nucleic acid molecule of claim 10 consisting of the nucleic acid sequence set forth in SEQ ID NO:1.

13. A replicable expression vector comprising a nucleic acid molecule encoding an isopentenyl monophosphate kinase, said nucleic acid molecule hybridizing to the nucleic acid molecule consisting of the sequence set forth in SEQ ID NO: 1, or the complement of the sequence set forth in SEQ ID NO: 1, under moderately stringent conditions, provided that said nucleic acid molecule does not consist of a nucleic acid sequence selected from the group consisting of SEQ ID NO:5, SEQ ID NO:9, SEQ ID NO:11 and SEQ ID NO:15.

14. A replicable expression vector of claim 13 comprising a nucleic acid sequence encoding a plant isopentenyl monophosphate kinase.

15. A host cell comprising a vector of claim 13.

16. A host cell comprising a vector of claim 14.

17. A method of altering the level of expression of isopentenyl monophosphate kinase in a host cell comprising introducing into said host cell a nucleic acid molecule encoding an isopentenyl monophosphate kinase under conditions that enable expression of said isopentenyl monophosphate kinase in said host cell, said nucleic acid molecule hybridizing to the nucleic acid molecule consisting of the sequence set forth in SEQ ID NO: 1, or the complement of the sequence set forth in SEQ ID NO: 1, under moderately stringent conditions.

18. The method of claim 17 wherein said host cell is a plant cell.

19. The method of claim 17 wherein said host cell is an animal cell.

20. The method of claim 17 wherein said host cell is a prokaryotic cell.

21. The method of claim 17 wherein said host cell is a yeast cell.

22. The method of claim 17 wherein said host cell is a fungal cell.

23. The method of claim 17 wherein the level of expression of isopentenyl monophosphate kinase in said host cell is enhanced.

* * * * *